United States Patent [19]

McCapra

[11] Patent Number: 5,283,334
[45] Date of Patent: Feb. 1, 1994

[54] SIDE-CHAIN FUNCTIONAL CHEMILUMINESCENT LABELS AND THEIR CONJUGATES, AND ASSAYS THEREFROM

[75] Inventor: Frank McCapra, Seaford, Great Britain

[73] Assignee: London Diagnostics, Inc., Eden Prairie, Minn.

[21] Appl. No.: 859,676

[22] Filed: Mar. 30, 1992

Related U.S. Application Data

[63] Continuation-in-part of Ser. No. 140,040, Dec. 31, 1987, abandoned, and Ser. No. 291,843, Dec. 29, 1988, abandoned, and Ser. No. 418,956, Oct. 10, 1989, abandoned.

[51] Int. Cl.$^5$ .................................. C07D 219/04
[52] U.S. Cl. ................................ 546/104; 436/501; 530/409; 544/355; 546/61; 546/79; 546/93; 546/102; 546/107; 546/108; 546/112; 546/147; 546/170; 548/309.4
[58] Field of Search .............. 546/79, 93, 102, 104, 546/107, 108, 61, 147, 112, 170; 544/355; 548/309.4; 436/501; 530/409

[56] References Cited

U.S. PATENT DOCUMENTS

| | | | |
|---|---|---|---|
| 3,352,791 | 11/1967 | Sheehan et al. | 546/102 X |
| 3,689,391 | 9/1972 | Ullman | 546/102 X |
| 4,745,181 | 5/1988 | Law et al. | 546/104 X |
| 4,918,192 | 4/1990 | Law et al. | 546/104 |
| 4,946,958 | 8/1990 | Campbell et al. | 546/104 |
| 4,950,613 | 8/1990 | Arnold et al. | 546/104 |
| 5,110,932 | 5/1992 | Law et al. | 546/102 |

FOREIGN PATENT DOCUMENTS

| | | | |
|---|---|---|---|
| 216553 | 4/1987 | European Pat. Off. | 546/102 |
| 324202 | 7/1989 | European Pat. Off. | 546/102 |
| 330050 | 8/1989 | European Pat. Off. | 546/104 |
| 361817 | 4/1990 | European Pat. Off. | 546/102 |
| 1461877 | 1/1977 | United Kingdom | 546/102 |

*Primary Examiner*—Richard L. Raymond
*Attorney, Agent, or Firm*—George A. Skoler

[57] ABSTRACT

A chemiluminescent compound possessing an aryl ester, thioester or amide of a carboxylic acid substituted heterocyclic ring or ring system that is susceptible to chemical attack to dissociate the heterocyclic ring to a transient compound. The heterocyclic ring is ring carbon-bonded to the carbonyl of the ester, thioester or amide moiety and possesses a heteroatom in an oxidation state that allows chemiluminescence by dissociating a compound at the carbon bonded to the carbonyl that decays to produce chemiluminescence. The heterocyclic ring or ring sustem contains bonded to it through an organic moiety, a functional group that is functionally reactive with an active hydrogen containing compound. The aryl ring is a ring or ring system that is ring carbon-bonded to the oxygen, sulfur or nitrogen of the ester, thioester or amide, as the case may be, and contains substituents on a six-member ring that act to sterically and electronically hinder hydrolysis of the ester, thioester or amide linkage. Optionally, there is an electron donating substituent in a peri position on the heterocyclic ring system. The substituents on the aryl ring comprise at least one ortho electron donating substitution that with the peri substitution comprises at least two substituents adjacent to the ester, thioester or amide linkage that are electron donors; at least one meta or para substituent on the aryl ring that possesses a $\sigma_p$ value greater than 0 and less than 1.

Also described are assays and assay kits that employ such label compounds.

42 Claims, No Drawings

SIDE-CHAIN FUNCTIONAL CHEMILUMINESCENT LABELS AND THEIR CONJUGATES, AND ASSAYS THEREFROM

RELATED APPLICATIONS

This application is a continuation-in-part of application Ser. No. 140,040, filed Dec. 31, 1987, now abandoned, and copending application Ser. No. 291,843, filed Dec. 29, 1988, now abandoned, and copending application Ser. No. 418,956, filed Oct. 10, 1989, now abandoned.

BRIEF DESCRIPTION OF THE INVENTION

This invention relates to unique chemiluminescent labeling compounds, conjugates containing associated versions of the labeling compounds, assays and kits for performing such assay utilizing the conjugates. The labeling compounds effect coupling to form conjugates by having functional coupling groups appended to the heterocyclic ring or ring system of aryl heterocyclic esters, thiolesters and amides.

BACKGROUND TO THE INVENTION

The literature describes classes of compounds that give off light or "luminesce" by reaction through chemical treatment. The compounds that have this capability are termed chemiluminescent materials. Their dissociation is typically caused by treatment with peroxide or molecular oxygen at high pH. Light is produced by the decay of the transient ("intermediate") structure formed by peroxide or molecular oxygen reaction at an $sp^2$ or $sp^3$ hybridized carbon in the compound that is part of a chain or a ring or ring system.

As the literature indicates, any series of reactions which produce the intermediate:

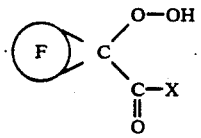

will lead to moderate to strong chemiluminescence. Ⓕ is a structure such that the product carbonyl derivative Ⓕ >C=O is fluoresent and X is a good leaving group, usually with XH, for efficient chemiluminescence, having a $pK_a$ of about $\leq 11$, preferably $<11$, and most preferably, from about 5 to about 8. The reaction may require base catalysis. The intermediate can be prepared (in isolable or transient form, depending on Ⓕ) from species such as:

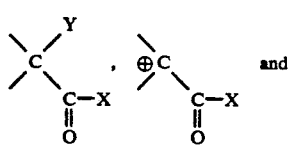

$H_2O_2$(Y is halogen, $-OSO_2R$, and the like) or

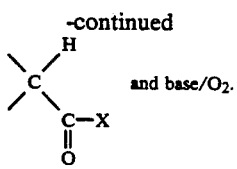

and base/$O_2$.

See *Endeavour*, 23, No. 117 (1973) p. 140, *The Chemistry of Bioluminescence* in "Bioluminescence in Action" (P. J. Herring, ed.), Academic Press, London, 1978 (pp. 64–5), *Proc. R. Soc. Lond.*, B 215, p. 256 (1982), *Progress in Organic Chemistry*, (W. Carruthers and J. K. Sutherland, eds.), Butterworth, London (1973), p. 261, all authored by F. McCapra.

For example, chemiluminescent aryl esters that contain such hybridized carbon, termed a labeling compound, react according to the following general reaction:

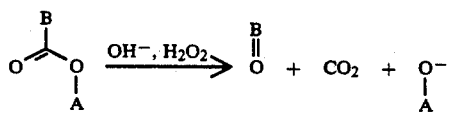

where A is an aryl ring or ring system and B is a heterocyclic ring or ring system. In this reaction, —O—A, the leaving group, is cleaved by perhydrolysis resulting in steps leading to the transient intermediate, B=O, that proceeds to decay generating luminescence.

The characteristics of some of these chemiluminescent compounds, their chemistry of manufacture, and other factors relating to them, are more fully described by McCapra, "Chemiluminescence of Organic Compounds," in Progress in Organic Chemistry, vol. 8, Carruthers and Sutherland ed., Wiley & Sons (1973); Kohen, Bayer, Wilechek, Barnard, Kim, Colleins, Beheshti, Richardson and McCapra, "Development Of Luminescence-Based Immunoassays For Haptens And For Peptide Hormones," pp. 149–158, in *Analytical Applications Of Bioluminescence and Chemiluminescence*, Academic Press, Inc. (1984); Richardson, Kim, Barnard, Collins and McCapra, *Clinical Chemistry*, vol. 31, no. 10, pp. 1664–1668 (1985); McCapra, "The Application of Chemiluminescence in Diagnostics," 40$^{th}$ Conference of the American Association of Clinical Chemists, New Orleans, La., Jul. 28, 1988; McCapra, "The Chemiluminescence Of Organic Compounds," Quarterly Reviews, vol. 20, pp. 485–510 (1966); McCapra, "The Chemiluminescence Of Organic Compounds," *Pure and Applied Chemistry*, vol. 24, pp. 611–629 (1970); McCapra, "The chemistry of bioluminescence," *Proceedings Of Royal Society*, vol. B215, pp. 247–278 (1982); McCapra and Beheshti, "Selected Chemical Reactions That Produce Light," *Bioluminescence and Chemiluminescence: Instruments and Applications*, CRC Press, vol. 1, Chapter 2, pp. 9–37 (1985); McCapra, "Chemiluminescent Reactions of Acridines," Chapt. IX, *Acridines*, R. M. Acheson, Ed., pp. 615–630, John Wiley & Sons, Inc. (1973); McCapra, "Chemical Mechanisms in Bioluminescence," *Accounts Of Chemical Research*, vol. 9, no. 6, pp. 201–208 (June 1976); and in many other publications and presentations on the subject.

As noted in the above literature, chemiluminescent compounds of a variety of structures have been projected as labels for a variety of assays including immunoassays (in this respect, see U.S. Pat. Nos. 4,383,031, 4,380,580 and 4,226,993). The esters, thiolesters and amides, alone or conjugated (i.e., chemically coupled to another material), are especially desirable forms of chemiluminescent labels. The function of chemiluminescent labels in assay applications involves the coupling of the label compound to a substrate molecule. Such coupling can be achieved by solvent interraction (e.g., molecular compatibility), any heterolytic or homolytic mechanism induced by chemical means and influenced by physical effects, such as time, temperature and/or mass action. For example, the reaction can be nucleophilic or electrophilic, or it can involve free radical mechanisms. In the broadest perspective, the coupling can be viewed as achievable via strong to weak bonding forces.

A chemiluminescent label in assays is an associated moiety of a binding material. The moiety is derived from a chemical compound which, as such, possesses chemiluminescent capabilities. Hereinafter, the term moiety as applied to the label as such, is a reference to the compound prior to being associated with a binding material. The term associated is intended to include all or any of the mechanisms for coupling the label to the substrate molecule.

The term "functional" in chemistry typically refers to a group that influences the performance of a chemical or constitutes the site for homolytic or heterolytic reactions. For example, a functional alkyl substituent, used in the context of interreactions through that substituent, means an alkyl group substituted so that it can effect that reaction. But an alkyl group termed functional for the electronic effects it induces in the molecule is a reference to the alkyl group per se.

In the context of the most favorable utilization of a chemiluminescent labeling compound, the compound should be designed to possess a functional group covalently associated therewith that is complementary to the functional group on the specific binding material or analyte to which it is to be attached for labeling purposes. The two functional groups are complementary such that when they interreact, the resulting label is covalently bonded to that substrate. For example, where the substrate's functional group contains an active hydrogen, then the functional group of the chemiluminescent label compound should be capable of reacting with it under appropriate reaction conditions to covalently bond to the substrate.

Chemiluminescent labels that utilize leaving groups that are hydrolytically attacked lose their luminescence capability over time in an aqueous system because they hydrolyze to products that are not available to the assay. Until recently, these compounds have not been used in commercial assays. Until this invention, the ester forms of this class of materials lacked sufficient hydrolytic stability to be stored in the most convenient form over an extended period of time, which is as a component of an aqueous system.

It is well understood in chemistry that carboxylic acid esters, thiolesters and amides are susceptible to hydrolytic attack resulting in the formation of the carboxylic acid and the hydroxy, mercapto or amino component that is the theoretical or actual precursor to the ester, thiolester or amide. Hydrolysis is more pronounced under acid or basic conditions. It is also recognized in chemistry that certain levels of hydrolysis can be inhibited by the inclusion of properly positioned bulky groups that chemically sterically hinder those linkages, see Nishioka, et al., *J. Org. Chem.*, vol. 40, no. 17, pp. 2520-2525 (1975), Fujita et al., "The Analysis of the Ortho Effect," *Progress in Physical Organic Chemistry*, 8, pp. 49-89 (1976), Morrison and Boyd, *Organic Chemistry*, 5th Ed., pp. 842-843 (1987) and March, *Advanced Organic Chemistry*, 3rd Ed., page 240 (1985). According to March:

"Another example of steric hindrance is found in 2,6-disubstituted benzoic acids, which are difficult to esterify no matter what the resonance or field effects of the groups in the 2 or the 6 position. Similarly, once the 2,6-disubstituted benzoic acids are esterified, the esters are difficult to hydrolyze."

(Emphasis in the original)

The difficulty in esterification is not the same in making esters from 2,6-substituted phenols, but the general principles described by March are applicable to enhancing the hydrolytic stability of the resultant ester so long as the ortho substitutions are electron donating. As this invention demonstrates, effective levels of hydrolytic stability require the presence of a select level of electron withdrawing chemical effect in conjunction with (and in addition to) traditional chemical steric hindrance factors.

The functional electron withdrawing or electron donating characteristics of a group in an organic compound is conventionally measured relative to hydrogen. This relative ranking accepts that all groups on a molecule will provide some electron withdrawing effect, and distinquishes them by the nature of impact the group has on the molecule's performance. An electron withdrawing functional group, characterized by a positive number, will draw electrons to itself more than hydrogen would if it occupied the same position in the molecule. The opposite occurs with an "electron donating group," a lesser electron withdrawing group which chemical convention characterizes by a negative number. Sigma para values ($\sigma_p$) are the relative measurement of electron withdrawing or electron donating qualities of a functional group in the para position on benzoic acid. See March, *Advanced Organic Chemistry*, 3rd Edition, Publ. by John Wiley & Sons, New York, N.Y. (1985) at pp. 242-250 and 617-8. Tables of $\sigma_p$ values for various groups can be found in Hansch et al., *J. Med. Chem.* 16(11):1209–1213 (1973) and Hansch and Leo, "Substituent Constants for Correlation Analysis in Chemistry and Biology," Ch, 6, pp. 49-52 (John Wiley & Sons, New York 1979). The $\sigma_p$ values reported in the Hansch articles are relied on herein in characterizing relative values for groups both in the meta and para position.

THE INVENTION

This invention relates to unique chemiluminescent labeling compounds, conjugates containing associated versions of the labeling compounds, assays and kits for performing such assay utilizing the conjugates. The labeling compounds contain special sterically-hindered aryl heterocyclic substituted esters, thiolesters and amides.

This invention relates to novel chemiluminescent labeling compositions and their conjugates with analytes and specific binding materials that are normally maintained in an aqueous medium. These compositions and the conjugates find special application in specific binding assays because the chemiluminescent compound, i.e., the labeled moiety, has increased and unique stability in aqueous mediums and exceptional luminating qualities.

The novel root compound of the invention is a chemiluminescent compound characterized by the presence an aryl ester, thiolester or amide of a carboxylic acid substituted heterocyclic ring or ring system that is susceptible to chemical attack (such as by oxidic attack) to form a transient compound from the heterocyclic ring. The heterocyclic ring is ring carbon-bonded to the carbonyl of the ester, thiolester and amide moiety and possesses a heteroatom in an oxidation state that allows chemiluminescence by dissociating a compound at the carbon bonded to the carbonyl ("intermediate") that decays to produce chemiluminescence. The heterocyclic ring or ring sustem contains bonded to it through an organic moiety, a functional group that is functionally reactive with an active hydrogen containing compound. The aryl ring is a ring or ring system that is ring carbon-bonded to the oxygen, sulfur or nitrogen of the ester, thiolester or amide, as the case may be, and contains substituents on a six-member ring that act to sterically and electronically hinder hydrolysis of the ester, thiolester or amide linkage. Optionally, there is an electron donating substituent in a peri position on the heterocyclic ring system. The substituents on the aryl ring comprise at least one ortho electron donating substitution that with the peri substitution comprises at least two substituents adjacent to the ester, thiolester or amide linkage that are electron donors; and at least one meta or para substituent directly attached to the aryl ring that possesses a $\sigma_p$ value greater than 0 and less than 1.

Also in accordance with the present invention are conjugates of the labeling composition, assay systems utilizing the conjugates, and assay kits incorporating such chemiluminescent labels.

In particular, this invention relates to an enhanced hydrolytically stable heterocyclic composition capable of chemiluminescent properties when labeled (i.e., affixed as a label) to an analyte or a specific binding material, by chemically-induced dissociation, comprising (a) an aryl ring,
(b) a sterically-hindered ester, thiolester or amide linkage moiety with enhanced hydrolytic stability, and
(c) a heterocyclic organic ring moiety, in which
(1) the carbonyl carbon of (b) is covalently bonded to a carbon atom (x) of (c) and the remaining free valence of (b) is carbon bonded to an aromatic ring carbon atom (y) of (a),
(2) (a) contains at least two substituent groups hindering hydrolysis of (b), at least one of which is electron donating and located on one or both ring carbon atoms adjacent to (y), the remaining substituent on (a) are meta or para to (y) and electron withdrawing with a $\sigma_p$ value greater than 0 and less than 1, and
(3) (c) contains
(i) at least one ring carbon atom adjacent to said ring carbon atom (x), a peri substituent on the ring carbon atom adjacent to said ring carbon atom (x) when there only one substituent on a ring carbon atom adjacent to (y),
(ii) an organic moiety directly bonded thereto that contains a functional group that is functionally reactive with an active hydrogen containing compound, and
(iii) a ring member heteroatom in an oxidation state that provides such chemiluminescence properties.

Also, this invention contemplates hydrolytically stable conjugates possessing chemiluminescent properties by chemical dissociation, comprising a chemiluminescent label bonded to a specific binding material or analyte that contains (a) an aryl ring,
(b) a sterically-hindered ester, thiolester or amide linkage moiety with enhanced hydrolytic stability, and
(c) a heterocyclic organic ring moiety, in which
(1) the carbonyl carbon of (b) is covalently bonded to a carbon atom (x) of (c) and the remaining free valence of (b) is carbon bonded to an aromatic ring carbon atom (y) of (a),
(2) (a) contains at least two substituent groups hindering hydrolysis of (b), at least one of which is electron donating and located on one or both ring carbon atoms adjacent to (y), the remaining substituent on (a) are meta or para to (y) and electron withdrawing with a $\sigma_p$ value greater than 0 and less than 1, and
(3) (c) contains
(i) at least one ring carbon atom adjacent to said ring carbon atom (x), a peri substituent on the ring carbon atom adjacent to said ring carbon atom (x) when there only one substituent on a ring carbon atom adjacent to (y),
(ii) an organic moiety directly bonded thereto that contains a functional group that is functionally reactive with an active hydrogen; containing compound, and
(iii) a ring member heteroatom that is in an oxidation state whereby reaction of molecular oxygen or a peroxide with said composition forms an intermediate which decays to produce chemiluminescence.

The invention encompasses a method for assaying the presence of an analyte in a sample. The method comprises conjugating an analyte or specific binding material with the aforementioned chemiluminescent labeled compound (the "conjugate"), effecting a binding assay of the analyte with the conjugate, inducing chemiluminescence by decay of an intermediate dissociated from the conjugate, and measuring luminescence therefrom to assay the analyte.

In keeping with the inventive chemiluminescent-label's function of assaying, the invention embodies a binding assay kit comprising a vial containing a conjugate possessing chemiluminescent properties by chemically induced dissociation and containing the aforementioned chemiluminescent label bonded to a specific binding material or analyte.

The invention recognizes that hydrolytic stability of a chemiluminescent label composition that utilizes aryl ester, thiolesters, and amides, as defined herein, linked to heterocyclic carboxy compounds, is affected by two factors. The first is the utilization of diortho substitution on the aryl ring of a kind that traditionally contributes to hydrolytic stability. This is the "bulky group" steric hindrance effect noted by Morrison and Boyd, supra. In the context of sigma values, these bulky groups are typically classed as electron donating. The second is the utilization of meta and/or para substitution on the same ring that untraditionally contributes to hydrolytic stability. This latter substitution possesses a $\sigma_p$ value greater than 0 and less than 1, as bonded to the ring. This combination of steric hindrance and positive $\sigma_p$ value provides materially superior hydrolytic stability to the labeling composition than substituents that possess a $\sigma_p$ value of 0 or less than 0, and 1 or more than 1.

By providing functional coupling attached to the heterocyclic ring or ring system, the invention opens up the variety of substituents bonded to the aryl group that beneficially affects the label's or the conjugate's hydrolytic stability. In addition, the combination of functional substitutions, electronically on the aryl group and reactive functionality on the heterocyclic ring or ring system, allows for coupling with groups most adept at binding to an analyte or a specific binding material, combined with aryl substituents that most favorably affect the hydrolytic stability of the label per se or conjugated.

DETAILED DESCRIPTION OF THE INVENTION

As mentioned above, proper positioning of bulky groups in an ester enhances the ester's hydrolytic stability. In the case of an aryl ester, steric hindrance is expected with bulky groups that block the ester moiety. Those groups may be provided on the aryl group in the ortho positions relative to the juncture with the ester moiety. Groups that may be dormant to any other reaction may not provide steric hindrance because of its chemical nature. For example, a group in a position alpha to a carbonyl moiety of an ester group that is electron withdrawing (such as an alpha chloro group) could adversely affect the hydrolytic stability of the ester group. However, a methyl electron donating group in the same position enhances hydrolytic stability. Thus, the relative position of the bulky group and its chemical nature is important to steric hindrance. As a result, the typical bulky group provided in the ortho position of an aryl ester for steric hindrance is electron donating. An electron withdrawing group would be expected to adversely affect the hydrolytic stability of the aryl ester. The presence of an electron withdrawing group substituted on an aryl ester would be expected to, to some degree, as a result of the field effects they introduce, reduce the hydrolytic stability of the ester, even if it is otherwise substituted with electron donating groups in the ortho positions. The presence of the electron withdrawing group would be expected to reduce the electron flow provided by the ortho electron donating groups to the ester group.

It has been surprising found that the presence of electron donating groups having a $\sigma_p$ value greater than 0 and less than 1, in aryl esters in positions meta and/or para to the ester linkage contribute significantly to the hydrolytic stability of the ester group. The following experiments demonstrates this point.

A small amount (about 0.1 mg) of a substituted phenyl ester of acridinium carboxylate fluorosulfonate chemiluminescent label, depicted in the following table, was dissolved in 100 μl of N,N-dimethylformamide (DMF). This solution was serially diluted (in the v/v ratio of 1:100) in a pH 6.0 phosphate buffer containing 0.4% BSA (bovine serum albumin) and 0.001% Thimerosal ®, as preservative. Chemiluminescent counts between 100,000 and about 400,000 were obtained. About 2 to 5 ml were incubated at 37° C. in a clear 5 ml vial capped with a rubber stopper and wrapped with Parafilm ®. Three 20 μl samples of each label were counted in a Berthold ® luminometer that was checked at various time intervals in the course of 14 days. The percent recovery of chemiluminescent counts after 14 days is set forth in the following table, as well as the relative ratio against a $\sigma_p$ value of 0:

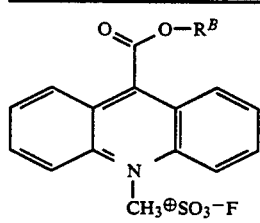

| $-R^B=$ | | % Recovery | Relative Ratio Against #7 | Sigma$_p$ Value |
|---|---|---|---|---|
| 1 | 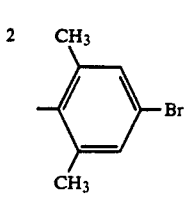 | 86 | 1.34 | 0.78 |
| 2 | CH$_3$ — ⟨ ⟩ — Br  CH$_3$ | 82 | 1.28 | 0.23 |

-continued

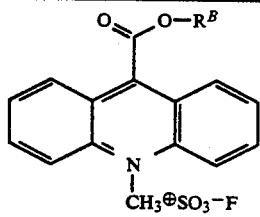

| -R$^B$ = | | % Recovery | Relative Ratio Against #7 | Sigma$_p$ Value |
|---|---|---|---|---|
| 3 | 2,4-dimethyl phenyl with SO$_2$NH-CH$_2$-C(O)O-benzyl at position 3 (CH$_3$ at 2,6; sulfonamide substituent) | 81 | 1.27 | 0.57 |
| 4 | 2,4,6-trimethyl phenyl with SO$_3^-$ | 76 | 1.19 | 0.09 |
| 5 | 3,5-dimethyl-4-methyl phenyl with C(O)O-benzyl | 72 | 1.13 | 0.45 |
| 6 | 3,5-dimethyl-4-methyl phenyl with CO$_2^-$ | 72 | 1.13 | 0.00 |
| 7 | 2,6-dimethyl phenyl | 64 | 1.00 | 0.00 |
| 8 | 3,5-dimethyl-4-methyl phenyl with -(CH$_2$)$_3$-C(O)O-benzyl | 69 | 1.08 | -0.07 |
| 9 | 2,4,6-trimethyl phenyl | 65 | 1.02 | -0.17 |

The data in the above table show the trend that significantly higher chemiluminescent count is obtainable with 2,6-dimethyl m or p substituted phenyl ester where the substitution has a $\sigma_p$ value greater than 0. Though compounds 3 and 8 differ materially in hydrolytic stability, they each contain large substituents in the meta or para position. In the case of compound 3, the sulfonamide linkage within the large substituent provides a high $\sigma_p$ value of 0.57, and in the case of compound 8, the propyl bridge to the ester contributes to electron donation, hence a $\sigma_p$ value of $-0.07$. With respect to compound 5, its high $\sigma_p$ value of 0.45 coupled with the % Recovery value strongly suggests that the ester hydrolyzed under the conditions of the experiment.

The chemiluminescent compounds of the present invention have the following schematic formula:

The chemiluminescent compounds of the present invention have the following schematic formula:

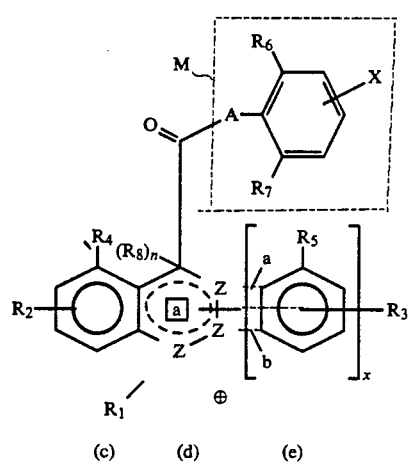

Formula "AB"

In this formula AB, ⓐ denotes the optional saturated or unsaturated nature of the internal heterocyclic ring shown in hatched lines. When n is 1, ⓐ is characterized by saturation, in which the ring in question is devoid of aromatic unsaturation. When n is 0, ⓐ is characterized by unsaturation, in which the ring in question is aromatically unsaturated. That distinction in unsaturation is further characterized by the following:

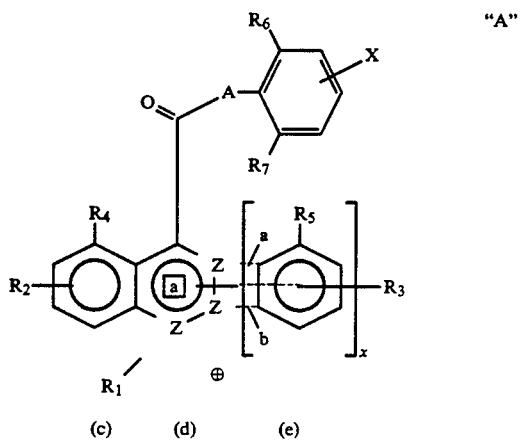

"A"

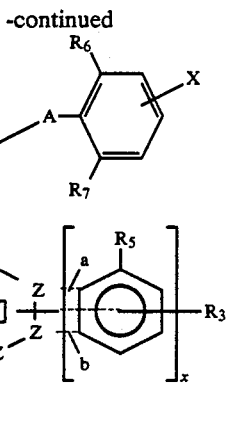

-continued "B"

In the above formulae "A" and "B", ⓐ characterize specific unsaturated (formula "A") or saturated (formula "B") forms. $R_8$ may be hydrogen. Formulas AB, as well as A and B, depict ring systems comprising at least two fused rings; in this case, rings designated "(c)", "(d)" and optionally "(e)". Two (2) of the Z's are carbon, and one (1) Z is nitrogen. Where the Z is carbon, it is bonded to one hydrogen unless it is part of a fused ring or contains a pendant group. Ring (e) may be a fused ring, in which case bonds a and b represent common carbons shared by both rings (d) and (e) and the proximate or adjacent Z's represent the shared carbons. Ring (e) may be a pendant ring attached to ring (d) by a convalent carbon to carbon bond represented by bonds a or b, depending upon where the pendancy occurs. The presence of ring (e) is determined by the value of x, which is either 0 or 1. M encompasses the leaving group comprising a portion of the linkage to the aryl group and the heterocyclic ring structure. M would be the leaving group even if X were conjugated to a specific binding material. The leaving group possesses the typical $pK_a$ of about $\leq 11$.

Peri substituents[1] that cause peri-interactions include any group that causes steric hindrance with respect to the carbon to which the ester, thiolester or amide linkage is attached and/or with respect to the carbon within the ester, thiolester of amide linkage. Preferred peri substituents include short alkyl groups ($C_{1-4}$, e.g., methyl, ethyl, and the like), aryl groups (e.g., phenyl), alkaryl (e.g., tolyl, xylyl, and the like), alkoxyalkyl ($C_{1-4}$ alkoxy, e.g., methoxymethyl, ethoxyethyl, and the like). The peri substituents, if present, are located on carbon atoms within the heterocyclic ring or ring system which are "adjacent to" the carbon to which the ester, thiolester or amide linkage is attached. Moieties can include more than one peri substituent. For example, peri substituents can be placed in the following positions:

(a) in acridiniums and acridans: on $C_1$ and $C_8$;

(b) in phenanthridiniums and reduced phenanthridiniums: on $C_7$; and (c) in quinoliniums and reduced quinoliniums: on $C_3$.

[1]Webster's Third New International Dictionary, Unabridged: "having substituents in or relating to positions 1 and 8 in two fused 6-membered rings (as in napthalene)"

Of the peri groups, $R_4$ and $R_5$ (when ring (e) is fused with ring (d)), $R_4$ is a bulky steric-hindering group and $R_5$ is a bulky steric-hindering groups or hydrogen. ($R_1$-) is an organo group that is carbon to nitrogen bonded to the Z that is nitrogen. $R_2$- and $R_3$- are functionally substituted organo groups or hydrogen bonded to ring carbon atoms of rings (c), (d) and (e), as the case may be, where the functionality is reactable with an active hydrogen containing group. At least one of $R_2$- and $R_3$- are such organo groups. Preferably, only one of $R_2$- and $R_3$- is such an organo group. When $R_2$- or $R_3$- are functionally substituted organo groups, they are bonded to ring carbon, preferably by a carbon to carbon bond, carbon to oxygen bond, carbon to nitrogen bond, carbon to sulfur bond, and the like. In addition, one of $R_2$- and $R_3$- may be amino, substituted amino, hydroxy, halogen, carboxy, or sulfonyl (and their esters) so long as the other is the functionally substituted organo group.

"A", in the above formulas, may be —O—, —S— or —NT—. T is a stable nitrogen bonded group such as —SO$_2$CF$_3$, to form —N(SO$_2$CF$_3$)—, and equivalent groups. Methods for forming such —NT— groups are described by Maulding et al., "Chemiluminescence from Reactions of Electrophilic Oxamides with Hydrogen Peroxide and Fluorescent Compounds," *J. Org. Chem.*, 33, 1, 250-254, (1968); Tseng et al., *J. Org. Chem.*, 44, 4113 (1979); Mohan, U.S. 4,053.430; Tseng et al., European Pat. Appln. 811 003 69.8 (1981); and European Pat. Applns. Pub. Nos. 0 273 115 and 0 257 541.

The aryl ring or ring system, represented by

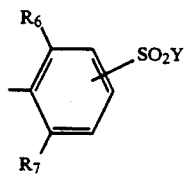

includes at least one substituted six-member ring of the formula

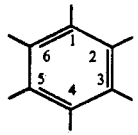

in which the substituents comprise a X at ring carbons 3, 4 or 5. The ester, amide or thiolester linkage is directly attached through a covalent bond to such six-member ring at ring carbon 1. The ring may include but is not limited to phenyl, naphthyl and anthracyl, which are derivatives of the following structures:

Phenylene

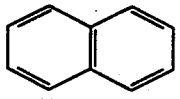
Naphthalene

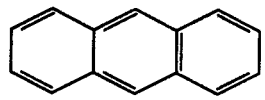
-continued
Anthracene

In those cases where napthyl or anthracyl rings are employed, one of the rings constitutes the phenyl shown and the other ring or rings are formed in combination with any adjacent set of ring carbons thereof other than carbon 1.

$R_6$ and $R_7$ are the classic bulky electron donating groups which are located on aryl group at $C_2$ and $C_6$ so as to sterically hinder, in the traditional manner, the hydrolysis of the linkage between aryl group and the heterocyclic ring or ring system. Where the aryl is phenyl with an ester linkage being attached at position 1, $R_6$ and $R_7$ are located at the ortho 2 and 6 positions. $R_6$ and $R_7$ may be the same or different, and either may include, when they are not hydrogen:

an alkyl or functionalized alkyl group
an aryl or functionalized aryl group
—OR, where R is alkyl or aryl
—SR, where R is alkyl or aryl.

Preferably, $R_6$ and $R_7$ may be hydrogen, alkyl ($C_{1-4}$), alkoxy ($C_{1-4}$) or alkyl sulfide ($C_{1-4}$), part of a fused ring system, with alkyl and alkoxy being preferred when one of $R_4$ or $R_5$ is hydrogen. More preferably, both $R_6$ and $R_7$ are bulky steric-hindering groups that are electron donating. One of $R_6$ and $R_7$ may be hydrogen so long as there is a sterically-hindering peri group present in at least one of $R_4$ and $R_5$ groups.

The required steric hindrance can also be provided by other rings within a multi-ring unit "adjacent" to the six-member ring to which the A group is attached. In such cases, the adjacent ring is considered, in the classic sense of steric hindrance, to be an electron donating substituent which sterically hinders the hydrolysis of the linkage.

X may be a variety of electron withdrawing groups, such as nitro, halogen, carboxy, carboxamido, sulfonamide, sulfonyl halide and the like, preferably having a $\sigma_p$ value greater than 0 and less than 1. The preferred groups are —NO$_2$, —SO$_2$Cl, —Br, and —N(CH$_3$)$_3$+. Most preferred are —NO$_2$ and —Br, because of the uniquely high hydrolytic stability they confer to the label, per se or when conjugated.

Covalent coupling the chemiluminescent label to a substrate is effected through reaction of functional groups contained in $R_1$, $R_2$ or $R_3$ that are complementary to the functional group(s) present in the substrate, e.g., the specific binding material or an analyte. In most cases, coupling will occur as a result of a nucleophilic reaction between the chemiluminescent label and the substrate resulting in chemical linkage of the chemiluminescent label to the substrate. The choice of chemical linkage is typically the result of the reaction of an organofunctional group on the substrate that contains an active hydrogen with a complementary functional group present in the chemiluminescent label compound that reacts with the active hydrogen containing group.

The choice of functional group is not narrowly critical. A suitable functional group is one that under the condition of the coupling reaction at least an aliquot of the label compound is reacted with the substrate and is coupled thereto. The coupling reaction involves either a nucleophilic substitution reaction or addition reaction between the functional group of the label and the functional group of the substrate. Such reactions are well known in the art.

Illustrative of such functional groups reactive with the active hydrogen containing group are the following:

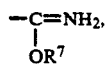

where $R^7$ is a residue of an alcohol

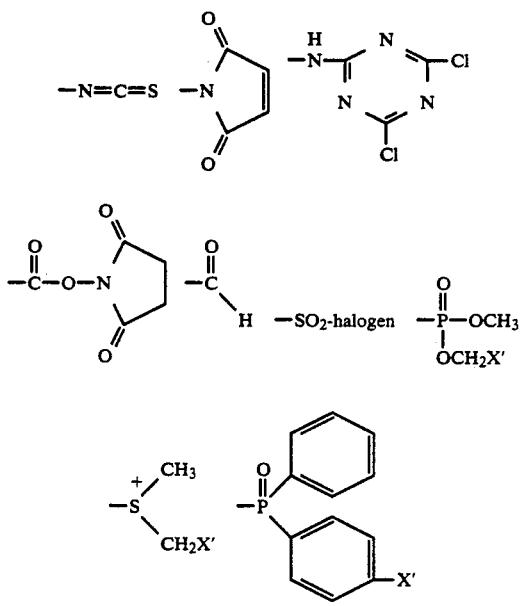

—$N_3$ and other photolabile functionalities in which halogen may be fluorine, chlorine, bromine and iodine, chlorine being the most preferred, and X' is a functional group reactive with active hydrogen, such as carboxyl halide, sulfonyl halide, amino and other groups known to be suitable for a linking reaction to proteins, nucleic acids and small molecule analytes. In addition, the functionality may be in the form of amino, mercapto, hydroxy, bonded to alkyl and aryl moieties. In the case of $R_{2 \ and \ 3}$ groups, they may comprise a variety of groups, such as those depicted as Q—$R_o$—B'—in the following formula:

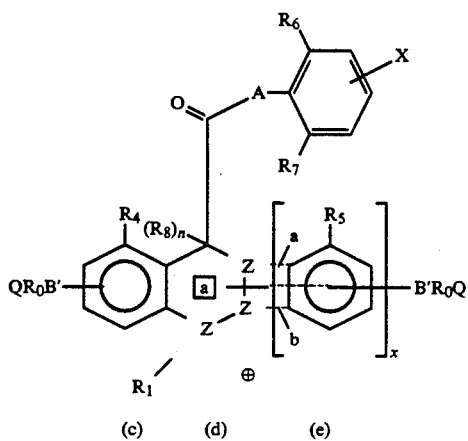

where B' is one of —O—, —CH—,

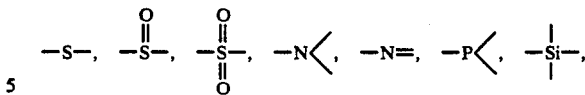

and the like. Q is a functional group such as defined above. —$R_0$— may be arylene, alkylene, alkenylene, alkynylene, cycloalkylene, the same groups coupled by an ester or ether group, to illustrate a few. In addition, one of the $R_{2 \ and \ 3}$ groups may contain an onium (such as quaternary ammoniums, phosphoniums, sulfoniums, and the like), sugar, polyalkylenepolyamine and polyalkyleneoxide (e.g., polyoxyethylene, polyoxy-1,2-propylene, polyoxy-1,3-propylene, polyoxy-1,2-butylene, etc.), and the like. For example, —$R_0$-may contain such groups as onium, alkylene oxy, and the like, as linkages for Q and B'. $R_1$ may comprise the functional group for coupling and in that case, it may comprise the composition of Q—$R_0$—B'-as depicted herein. Other chains, groups and functionalities useful for attaching compounds of the present invention via $R_{1, \ 2 \ or \ 3}$ group reactions to protein are discussed in Ji, "Bifunctional Reagents," Meth. Enzymology 91:580 (1983), which is incorporated herein by reference. Methods of joining such attaching groups to protein and other materials utilize both covalent bonding and weaker chemical forces, and are well known in the art.

In addition, one of $R_1$, $R_2$, and $R_3$ may comprise organo groups that provide a number of advantages, such as operating as surface active agents in compatibilizing the label compound or its conjugate in aqueous medium or to antigen structures. For example, they may comprise —$(CH_2CH_2O)_nY$, where n=1-10, and Y can be hydrogen, alkyl, and the like.

The label compounds of formula AB, including formulae A and B, comprise a heterocyclic ring (d) or ring system (c), (d) and (e) to which the ester, thiolester or amide linkage —CO—A— is attached at a carbon atom within the heterocyclic ring or ring system. That carbon atom (1) is either $sp^2$ or $sp^3$ hybridized, as shown in the two formulas, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is $sp^2$ hybridized, the heteroatom is in a positive oxidation state (i.e., have a positive charge, for example, as obtained by N-alkylation or N-oxidation). If the carbon to which the linkage is attached is $sp^3$ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

The label compounds of formula AB, including formulae A and B, comprise a heterocyclic ring (d) or ring system (c), (d) and (e) to which the ester, thiolester or amide linkage —CO—A— is attached at a carbon atom within the heterocyclic ring or ring system. That carbon atom (1) is either sp² or sp³ hybridized, as shown in the two formulas, and (2) is susceptible to attack by peroxide or molecular oxygen to form the intermediate that decays to produce chemiluminescence. The oxidation state of the heteroatom within the heterocyclic ring or ring system will determine whether the carbon atom is susceptible to such attack. If the carbon to which the linkage is attached is sp² hybridized, the heteroatom is in a positive oxidation state (i.e., have a positive charge, for example, as obtained by N-alkylation or N-oxidation). If the carbon to which the linkage is attached is sp³ hybridized, the heteroatom is in a neutral oxidation state (i.e., uncharged). When the heteroatom is nitrogen, proper oxidation states can be achieved only if the nitrogen is substituted with an alkyl group (including a reactive functionalized alkyl group), an aryl group (including a reactive functionalized aryl group), —O— (if the nitrogen is in a positive oxidation state) or —OH (if the nitrogen is in a neutral oxidation state). When the heteroatom is in these "proper" oxidation states, the carbon atom will be susceptible to attack by peroxide or molecular oxygen to produce the chemiluminescent intermediate.

Heterocyclic rings or ring systems that contain the heteroatom in a positive oxidation state include without limitation the following fused ring systems: acridinium, benz[a]acridinium, benz[b]acridinium, benz[c]acridinium, a benzimidazole cation, quinolinium, isoquinolinium, quinolizinium, a cyclic substituted quinolinium, phenanthridinium, and quinoxalinium. Rings or ring systems in which the heteroatom is in a neutral oxidation state include the reduced forms of the foregoing. These rings or ring systems are derived from the following rings or ring systems:

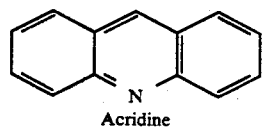
Acridine

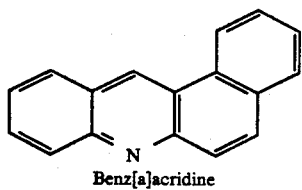
Benz[a]acridine

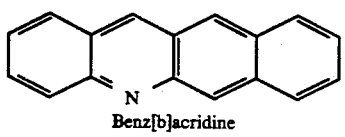
Benz[b]acridine

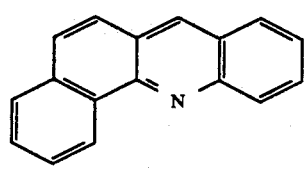
Benz[c]acridine

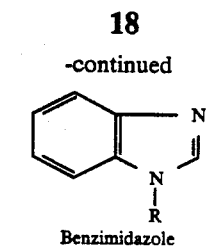
Benzimidazole

Quinoline

Isoquinoline

Quinolixinium Cations

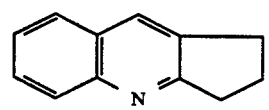

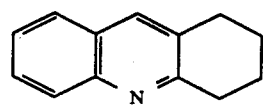

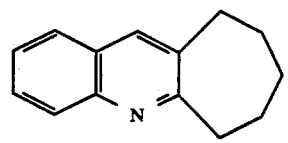
Cyclic C3, C4, C5-Substituted Quinolines

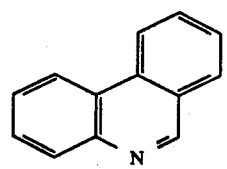
Phenanthridine

Quinoxaline

The above-described improved chemiluminescent compounds are useful in a broad range of specific binding assays for the presence of analyte in a sample. "Presence" shall mean herein the qualitative and/or quantitative detection of an analyte. Such assays may be directed at any analyte which may be detected by use of the improved chemiluminescent compound in conjunction with specific binding reactions to form a moiety thereon. These assays include, without limitation, immunoassays, protein binding assays and nucleic acid hybridization assays.

In a typical immunoassay, the analyte is immunoreactive and its presence in a sample may be determined by virtue of its immunoreaction with an assay reagent. In a typical protein binding assay, the presence of analyte in a sample is determined by the specific binding reactivity of the analyte with an assay reagent where the reactivity is other than immunoreactivity. Examples of this include enzyme-substrate recognition and the binding affinity of avidin for biotin. In the typical nucleic acid hybridization assay, the presence of analyte in a sample is determined by a hybridization reaction of the analyte with an assay reagent. Analyte nucleic acid (usually present as double stranded DNA or RNA) is usually first converted to a single stranded form and immobilized onto a carrier (e.g., nitrocellulose paper). The analyte nucleic acid may alternatively be electrophoresed into a gel matrix. The immobilized analyte may then be hybridized (i.e., specifically bound) by a complementary sequence of nucleic acid.

The foregoing specific binding assays may be performed in a wide variety of assay formats. These assay formats fall within two broad categories. In the first category, the assay utilizes a chemiluminescent conjugate which comprises the improved chemiluminescent moiety attached to a specific binding material. "Specific binding material" means herein any material which will bind specifically by an immunoreaction, protein binding reaction, nucleic acid hybridization reaction, and any other reaction in which the material reacts specifically with a restricted class of biological, biochemical or chemical species. In this category of assays, the chemiluminescent conjugate participates in a specific binding reaction and the presence of analyte in the sample is proportional to the formation of one or more specific binding reaction products containing the chemiluminescent conjugate. The assay is performed by allowing the requisite specific binding reactions to occur under suitable reaction conditions. The formation of specific binding reaction products containing the chemiluminescent conjugate is determined by measuring the chemiluminescence of such products containing the chemiluminescent conjugate or by measuring the chemiluminescence of unreacted or partially reacted chemiluminescent conjugate not contained in such products.

This first category of assay formats is illustrated by sandwich assays, competitive assays, surface antigen assays, sequential saturation assays, competitive displacement assays and quenching assays.

In a sandwich format, the specific binding material to which the chemiluminescent moiety is attached, is capable of specifically binding with the analyte. The assay further utilizes a reactant which is capable of specifically binding with the analyte to form a reactant-analyte-chemiluminescent conjugate complex. The reactant may be attached to a solid phase, including without limitation, dip sticks, beads, tubes, paper or polymer sheets. In such cases, the presence of analyte in a sample will be proportional to the chemiluminescence of the solid phase after the specific binding reactions are completed. Such assay formats are discussed further in U.S. Pat. Nos. 4,652,533, 4,383,031, 4,380,580 and 4,226,993, which are incorporated herein by reference.

In a competitive format, the assay utilizes a reactant which is capable of specifically binding with the analyte to form an analyte- reactant complex and with the specific binding material, to which the chemiluminescent moiety is attached, to form a chemiluminescent conjugate-reactant complex. The reactant may be attached to a solid phase, or alternatively reaction products containing the reactant may be precipitated by use of a second antibody or by other known means. In this competitive format, the presence of analyte is "proportional," i.e., inversely proportional, to the chemiluminescence of the solid phase or precipitate. A further discussion of this assay format may be found in the immediately above mentioned U.S. patents.

In another assay format, the analyte may occur on or be bound to a larger biological, biochemical or chemical species. This type of format is illustrated by a surface antigen assay. In this format, the specific binding material is capable of specifically binding with the analyte and the presence of analyte is proportional to the analyte-chemiluminescent conjugate complex formed as a reaction product. This is illustrated by attaching the chemiluminescent moiety to an antibody which is specific to a surface antigen on a cell. The presence of the cell surface antigen will be indicated by the chemiluminescence of the cells after the completion of the reaction. The cells themselves may be used in conjunction with a filtration system to separate the analyte-chemiluminescent conjugate complex which is formed on the surface of the cell from unreacted chemiluminescent conjugate. This is discussed further in U.S. Pat. No. 4,652,533.

The improved chemiluminescent moiety may be used in additional assay formats known in the art including without limitation sequential saturation and competitive displacement, both of which utilize a chemiluminescent conjugate where both (1) the specific binding material, to which the moiety is attached, and (2) the analyte specifically bind with a reactant. In the case of sequential saturation, the analyte is reacted with the reactant first, followed by a reaction of the chemiluminescent conjugate with remaining unreacted reactant. In the case of competitive displacement, the chemiluminescent conjugate competively displaces analyte which has already bound to the reactant.

In a quenching format, the assay utilizes a reactant which is capable of specifically binding with the analyte to form an analyte-reactant complex and with the specific binding material, to which the chemiluminescent moiety is attached, to form a chemiluminescent conjugate-reactant complex. A quenching moiety is attached to the reactant. When brought into close proximity to the chemiluminescent moiety, the quenching moiety reduces or quenches the chemiluminescence of the chemiluminescent moiety. In this quenching format, the presence of analyte is proportional to the chemiluminescence of the chemiluminescent moiety. A further discussion of this format may be found in U.S. Pat. Nos. 4,220,450 and 4,277,437, which are incorporated herein by reference.

In consideration of the above discussed assay formats, and in the formats to be discussed below, the order in which assay reagents are added and reacted may vary widely as is well known in the art. For example, in a sandwich assay, the reactant bound to a solid phase may be reacted with an analyte contained in a sample and after this reaction the solid phase containing complexed analyte may be separated from the remaining sample. After this separation step, the chemiluminescent conjugate may be reacted with the complex on the solid phase. Alternatively, the solid phase, sample and chemiluminescent conjugate may be added together simultaneously and reacted prior to separation. As a still further but less preferred alternative, the analyte in the sample and the chemiluminescent conjugate may be reacted prior to addition of the reactant on the solid phase. Similar variations in the mixing and reaction steps are possible for competitive assay formats as well as other formats known in the art. "Allowing under suitable conditions substantial formation" of specific binding reaction products shall herein include the many different variations on the order of addition and reaction of assay reagents.

In the second category of assay formats, the assay utilizes an unconjugated improved chemiluminescent compound. The presence of analyte in the sample is proportional to the formation of one or more specific binding reaction products which do not themselves contain the chemiluminescent moiety. Instead, the chemiluminescent compound chemiluminesces in proportion to the formation of such reaction products.

In one example of this second category of assays, the assay utilizes a reactant capable of binding with the analyte to form an analyte-reactant complex which causes the chemiluminescent compound to chemiluminesce. This is illustrated by a simple enzyme-substrate assay in which the analyte is the substrate glucose and the reactant is the enzyme glucose oxidase. Formation of the enzyme-substrate complex triggers the chemiluminescent compound. Such enzyme-substrate assay for glucose is disclosed in U.S. Pat. Nos. 3,964,870 and 4,427,770, both of which are incorporated herein by reference. This enzyme-substrate assay is a specific binding assay in the sense that the substrate specifically binds to the active site of the enzyme in much the same way that an antigen binds to an antibody. In this assay, the enzyme specifically binds with the substrate which results in the production of peroxide which, in turn, causes the chemiluminescent compound to chemiluminesce.

Also included in the second category of assays are those assays in which the formation of the reaction products promotes or inhibits chemiluminescence by the chemiluminescent compound in a less direct manner. In this assay, a first reactant, which is cross reactive with the analyte, is attached to an enzyme such as glucose oxidase close to its active site. A second reactant which is specific for both the analyte and the immunoreactive material is added to the sample and the altered enzyme in the presence of the substrate (i.e., glucose). When the second reactant binds to the first reactant located near the active site on the enzyme, the second reactant blocks the active site in a way that the substrate cannot bind to the enzyme at the active site or the binding of the substrate at the active site is significantly decreased. The second reactant blocking the enzyme in this manner inhibits the enzyme from producing peroxide which, in turn, would have triggered the chemiluminescent moiety. Analyte in the sample, however, will tie up the second reactant, thus preventing the second reactant from inhibiting the production of peroxide. The presence of analyte will be proportional to the chemiluminescence of the compound.

The assays contained in the above two categories of assay formats may be heterogeneous or homogeneous. In heterogeneous assays, the reaction products, whose formation is proportional to the presence of analyte in the sample, are separated from other products of the reaction. Separation can be achieved by any means, including without limitation, separation of a liquid phase from a solid phase by filtration, microfiltration, double antibody precipitation, centrifugation, size exclusion chromatography, removal of a solid phase (e.g., a dip stick) from a sample solution or electrophoresis. For example, in a sandwich assay the reactant-analyte-chemiluminescent conjugate complex is separated from unreacted chemiluminescent conjugate. In a surface antigen assay, the analyte-chemiluminescent conjugate complex is separated from unreacted chemiluminescent conjugate. In a competitive assay, the reactant-chemiluminescent conjugate ocmplex is separated from unreacted chemiluminescent conjugate. In a sequential saturation assay and in a competitive displacement assay, the reactant-chemiluminescent conjugate complex is separated from unreacted chemiluminescent conjugate. Alternatively, in homogeneous assays the reaction products are not separated. After the assay reagents have been allowed to react, the chemiluminescence may be measured from the whole assay mixture whether such mixture is in solution, on a solid phase or distributed between various membrane layers of a dip stick or other solid support. The glucose assay using glucose oxidase and a chemiluminescent moiety illustrates a simple homogeneous assay in which separation is unnecessary. The quenching assay illustrates a more complex homogeneous assay in which separation is unnecessary. It is contemplated that either category of assay formats may give rise to either heterogeneous or homogeneous formats.

Finally, "measuring the chemiluminescence" shall include, where relevant, the act of separating those specific binding reaction products, the formation of which are proportional to the presence of analyte in the sample, from other reaction products. It shall also include, where relevant, the acts of triggering the chemiluminescent moiety to chemiluminesce in the case of those assay formats in which the formation of the reaction products does not itself trigger the chemiluminescent moiety.

SYNTHESIS OF MOIETIES

The following examples show the synthesis of certain chemiluminescent moieties of the present invention. These chemiluminescent moieties are typically made in small quantities and the procedures employed for their manufacture do not reflect conventional large scale chemical manufacturing procedures. In these reactions, conventional reactions have been employed to produce the chemiluminescent labels of the invention. Purification procedures suitable for isolating product are conventional laboratory procedures, such as crystallization out of solvent solution by the addition of a nonsolvent, solvent extraction, and the like. In such cases, many different solvents and nonsolvents are suitable. Yields are the amounts recovered as a percentage of reactants employed.

EXAMPLE 1

An illustrative chemiluminescent compound of the present invention is (2,6-dimethyl-4-nitro)phenyl-3-(3-succinimidyl-oxycarbonyl) propyloxy-N-methyl-acridinium-9-carboxylate fluorosulfonate (or other counter ions such as chloride, trifluoroacetate, sulfate, etc.) which has the following formula:

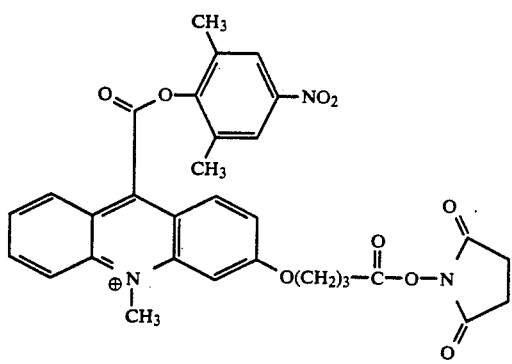
The compound (2,6-dimethyl-4-nitro) phenyl-3-(3-succinimidyl-oxycarbonyl) propyloxy-N-methyl-acridinium-9-carboxylate fluorosulfonate was synthesized according to the following scheme:
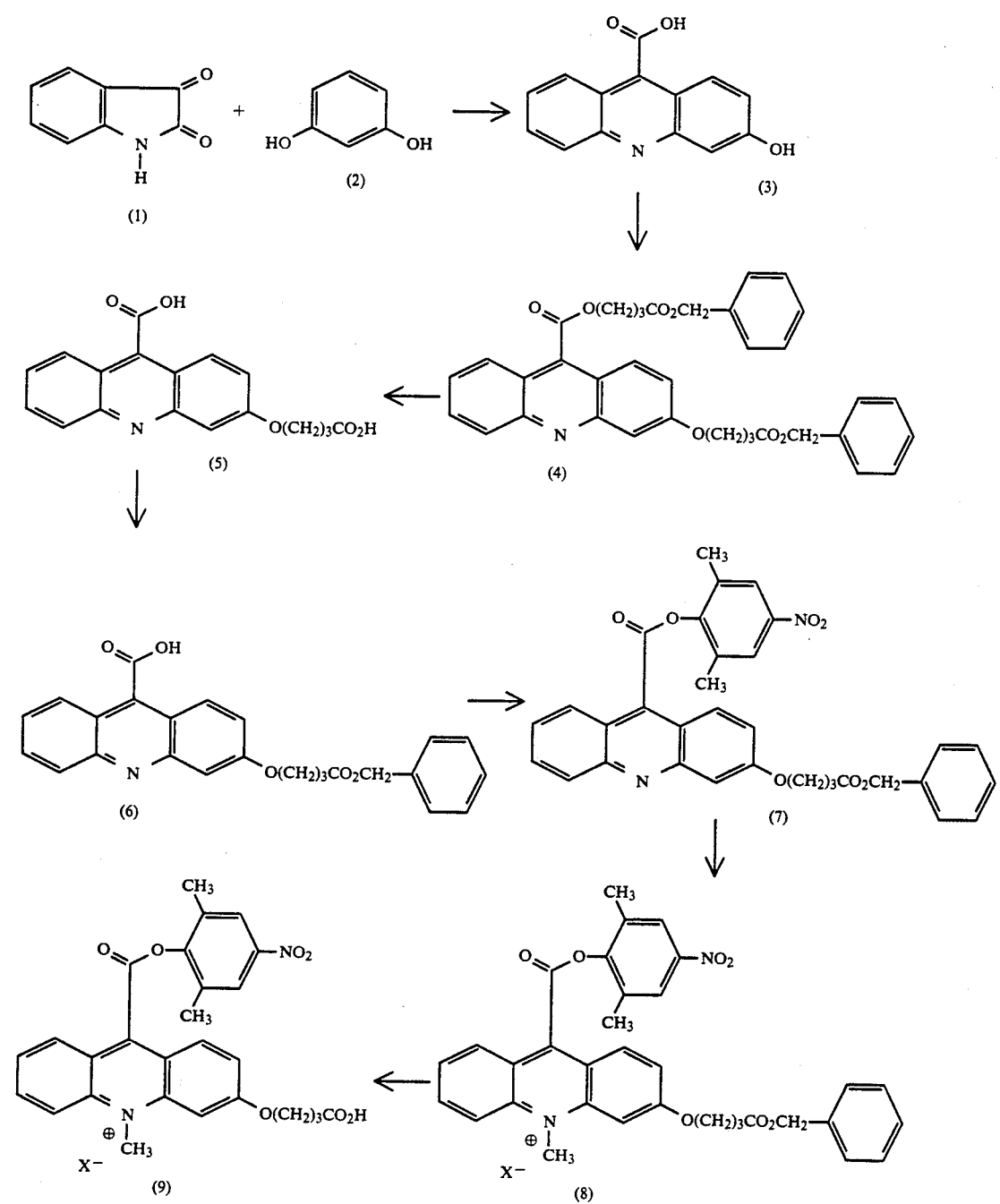

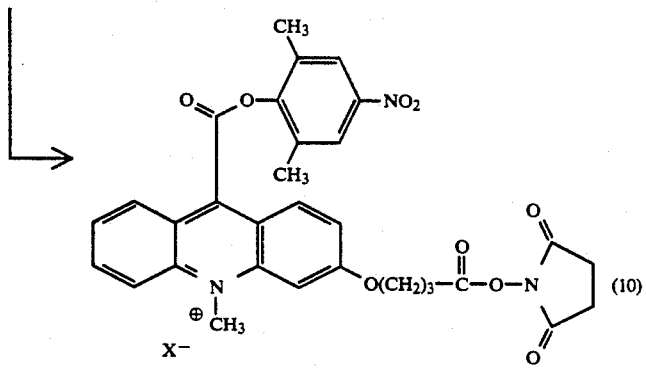

Condensation of isatin (1) with resorcinol (2) provides the 3-hydroxy acridine-9-carboxylic acid (3). Reaction with benzyl-4-bromo butyrate gives the ester (4) with the 3-hydroxy group etherified. Hydrolysis using base removes both the benzyl groups resulting in the dicarboxylic acid (5). Selective rebenzylation of the carboxylic function of the propyloxy group gives 9-carboxylic acid (6). Esterification with 2,6-dimethyl-4-nitrophenol yields (7) and methylation of the acridine nitrogen gives (8). Deprotection of the carboxyl group with HBr provides (9) and condensation with N-hydroxysuccinimide using DCC provides (2,6-dimethyl-4-nitro) phenyl-3-(3-succinimidyl-oxycarbonyl) propyloxy-N-methyl-acridinium-9-carboxylate fluorosulfonate (10). These reactions are described in further detail in the following.

In the first step, 4-bromobutyryl chloride (13.8 g, 75 mmole) was placed in a 100 ml round bottom flask. The flask was cooled to −20° C. using a dry ice/carbon tetrachloride bath. Ethyl acetate (50 ml) containing N-methylmorpholine (7.58 g, 75 mmole, 8.2 ml) was added carefully. Using an addition funnel, benzyl alcohol (6.97 g, 6.67 ml, 6.64 mmoles) was added dropwise. After the addition the bath was removed and the mixture was stirred for 2 hours. The product was transferred to a separatory funnel using ethyl acetate (50 ml), washed once with sodium bicarbonate (10%), then twice with water, and dried with anhydrous sodium sulfate. Evaporation of solvents gave benzyl-4-bromobutyrate as an oil (yield=91%).

Isatin (1) (1.88 g) was slowly added to a solution of potassium hydroxide (5.07 g, 0.09 mole) dissolved in water (3.5 ml). The reaction flask was heated to about 50° C. in an oil bath. About 10 ml more water was added dropwise. Resorcinal (2) (10 g, 0.089 mole) was added and the temperature was raised to 100° C. as stirring was continued, resulting in the formation of a molten mixture. More isatin (1) (1.88 g) was added. The reaction flask (3-necked round bottom) was attached to a nitrogen inlet and the water vapors were flushed out by the stream of nitrogen. The mixture was stirred for 4 hours at 125° C. Water (70 ml) was added and the contents were dissolved by continued stirring. After transferring the mixture to an erlenmeyer flask the volume was brought up to 200 ml with water. The pH was adjusted to 2.0 with concentrated hydrochloric acid. Filtration and washing of the solids with water gave the crude acridine acid. It was then dissolved in 2N NaOH (100 ml) and the solution was filtered through celite. The celite bed was washed with 200 ml of 1N NaOH. The filtrate was acidified with concentrated HCl to pH 2.0. The precipitate of 2-hydroxy-acridine-9-carboxylic acid (3) was filtered, washed with water and was dried in vacuum over $P_2O_5$ (yield=42%).

In the next sequence, 3-hydroxy-9-acridine carboxylic acid (3) (4 g, 0.017 mole), benzyl-4-bromobutyrate (14.6 g, 0.057 mole) and cesium carbonate (22.16 g, 0.068 mole) were dissolved in DMSO (125 ml) in a 250 ml round bottom flask. The flask was warmed to about 50° C. in an oil bath. After stirring the mixture at that temperature for 1 hour, the mixture was poured into water (1 liter). The precipitated product was extracted with chloroform after making the aqueous suspension basic with sodium bicarbonate. Drying and evaporation of chloroform gave 3-(3-benzyloxycarbonyl)-propyloxy-9-(3-benzyloxy-carbonyl-propyl) acridine carboxylate (4) which was chromatographed on a silica gel column using chloroform as solvent. Fractions with $R_f$ value of 0.36 on TLC with $CHCl_3$/EtOAc, 9/1, were pooled. The solvents were evaporated (yield=55%).

Then, 3-(3-benzyloxycarbonyl)-propyloxy-9-(3-benzyloxycarbonyl propyl) acridine carboxylate (4) (4.93 g, 8.3 mmole) was added to a mixture of 2N NaOH (300 ml) and methanol (300 ml). The mixture was stirred at room temperature for 48 hours. The methanol was removed on a rotary evaporator and the solution was acidified with concentrated hydrochloric acid to pH 6.0. The precipitated solids were filtered, washed with water and dissolved in ethyl acetate. The solution was dried and then the solvents were evaporated to give 3-(3-carboxy) propyloxy-acridine-9-carboxylic acid (5) (yield=92.8%).

This compound, 3-(3-carboxy) propyloxy-acridine-9-carboxylic acid (5) (1.5 g, 4.6 mmole), was dissolved in DMAP (80 ml, 1,3-dimethyl-3,4,5,6-tetrahydro-2(IH)-pyrimidone) with warming. Benzyl alcohol (0.5 ml, 0.52 g, 4.8 mmole), 1,3-dicyclohexylcarbodiimide (1.04 g, 5.0 mmole) and N,N-dimethyl aminopyridine (0.2 g, 1.6 mmole) were added to the reaction which was previously cooled in a bath of dry ice/$CCl_4$. The mixture was stirred for 15 hours with a nitrogen inlet at room temperature. The mixture was added to saturated sodium chloride (320 ml). 3-(3-benzyloxycarbonyl) propyloxy-acridine-9-carboxylic acid (6) was filtered and was washed with a small amount of water. The product was chromatographed on a silica gel column using $CHCl_3$/MeOH, 95/5 as solvent (yield=26%).

The compound 3-(3-benzyloxycarbonyl) propyloxy-acridine-9-carboxylic acid (6) (0.5 g, 1.2 mmole) and p-toluene sulfonyl chloride (0.46 g, 2.4 mmole) were dissolved in pyridine (20 ml). The solution was cooled in a bath of dry ice/$CCl_4$ for 15 minutes. 2,6-dimethyl-4-nitrophenol (0.2 gm, 1.2 mmole) was added and the cooling bath was removed and the mixture was stirred for 15 hours at room temperature. It was added to water (450 ml) and the pH was adjusted to 2.0 with concentrated hydrochloric acid. The product was filtered, washed with water and was dried in vacuum. The crude product was chromatographed on a silica gel column using chloroform as solvent. Fractions with an $R_f$ value of 0.8 on TLC with $CHCl_3/EtOAc$, 1:1, were pooled. Evaporation of solvents gave (2,6-dimethyl-4-nitro)-phenyl-3-(3-benzyloxycarbonyl)-propyloxy-acridine-9-carboxylate (7) (yield=47%).

The acridine (7) (0.32 g, 0.56 mmole) was dissolved in anhydrous methylene chloride (4 ml) and methyl fluorosulfate (0.27 ml, 3.36 mmole, 6 molar equivalent) was added. The mixture was stirred for 15 hours at room temperature. Anhydrous ether (20 ml) was added. (2,6-dimethyl-4-nitro)phenyl-3-(3-benzyloxycarbonyl)-propyloxy-acridinium-9-carboxylate fluorosulfonate (8) was filtered and washed with ether (50 ml). The yield was quantitative.

The benzyl-protected acridinium ester (8) (250 ng) was treated with 30% HBr/Acetic acid (3 ml) for 2 hours at 55° C. Anhydrous ether (20 ml) was added to precipitate the product. Filtration and washing of the solids with ether gave (2,6-dimethyl-4-nitro)phenyl-3-(3-carboxyl)propyloxy-acridinium-9-carboxylate fluorosulfonate (9). Crystallization from acetonitrile provided the pure compound (yield=80%). Purification by crystallization from other solvents achieves equivalent results. The same results may be achieved by crystallization from acetonitrile by the addition of ethyl acetate. Other useful solvent combinations include alcohol and ether, such as methanol, ethanol or propanol and diethyl ether (ether is the precipitating solvent).

The deprotected acridinium (9) (67 mg, 0.13 mmole) in a 50 ml 2-necked round bottom flask was dissolved in anhydrous acetonitrile (10 ml). Dicyclohexylcarbodiimide (DCC, 33 mg, 0.16 mmole) was added and the mixture stirred for 45 minutes at room temperature. N-hydroxysuccinimide (17 mg, 0.15 mmole) was added and reaction continued for 2.5 hours. More DCC (14 mg) and N-hydroxysuccinimide (8 mg) were added and followed again by the same amounts after 1.5 hours. After 1.5 hours after the last addition, glacial acetic acid (1.7 ml) was added to quench excess DCC. The solvent was removed in vacuo.

The crude product was purified on a semi-preparative $C_{18}$-Dynamax HPLC column (commercially available from Rainin Instrument Co., Inc., Woburn, Mass.) using $CH_3CN/H_2O$ (0.1% Trifluoroacetic acid) 60/40, as the mobile phase at a flow rate of 1.8 ml/min, using 360 nm for detection. The fraction at retention time 9.4 minutes was collected and the solvents were removed in vacuo. The (2,6-dimethyl-4-nitro)-phenyl-3-(3-succinimidyl-oxycarbonyl) propyloxy-acridinium-9-carboxylate fluorosulfonate (10) was dried under vacuum in a dessicator containing phosphorus pentoxide (yield=33%). MS: FAB, thioglycerol matrix, 586 (M+). HPLC: Rainin $C_{18}$ Dynamax (10 mm×25 mm), $CH_3CN/H_2O$ (0.1% trifluoroacetic acid), 60:40, flow rate 1.8 ml/min, retention time 9.4 min, detected at 360 nm.

EXAMPLE 2

Further illustrative of the present invention is (2,6-dimethyl-4-nitro)phenyl-3-(3-succinimidyloxycarbonyl) propyloxy-9,10-dihydro-N-methyl-acridan-9-carboxylate which has the following formula:

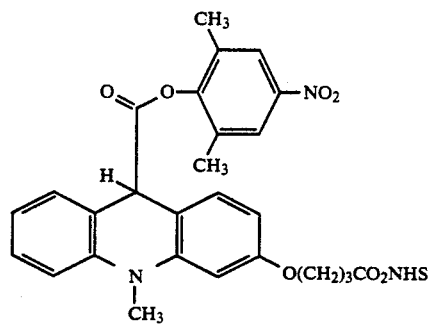

The compound (2,6-dimethyl-4-nitro)phenyl-3-(3-succinimidyloxycarbonyl) propyloxy-9,10-dihydro-N-methyl-acridan-9-carboxylate was synthesized from the acridinium acid (9). Reduction of the acid (9) with sodium cyanoborohydride gives the acridan which is then converted to the NHS ester by the mixed anhydride method. These reactions are described in further detail in the following.

The acridinium acid (9) (210 mg, 0.37 mmole) was dissolved in a 1:1 mixture of acetonitrile and 0.1M phosphate buffer, pH 5.2 (60 ml). A solution of sodium cyanoborohydride (190 mg) in acetonitrile (5 ml) was added dropwise to the acridinium solution. This results in the bleaching of the yellow color of the solution. Stirring was continued for 15 minutes. Acetonitrile (100 ml) was added and the solvents were removed in a rotary evaporator. The residue as a suspension in water is extracted with ethylacetate. The organic layer was washed with water and dried. Removal of solvents gave (2,6-dimethyl-4-nitro)phenyl-3-(3-carboxyl)propyloxy-9,10-dihydro-acridan-9-carboxylate (yield=90%).

The acridan acid (125 mg, 0.255 mmole) and N-methylmorpholine (28 1) were dissolved in anhydrous acetonitrile (15 ml). The mixture was cooled in a $CCl_4$/dry ice bath under nitrogen. Isobutylchloroformate (35 μl) was added, the mixture was stirred for 3 minutes and N-hydroxysuccinimide (35 mg) dissolved in acetonitrile (2 ml) was added. After stirring at −20° C. for 15 minutes the $CCl_4$/dry ice bath was removed and the reaction allowed to warm up to room temperature. After 2 hours the solvents were evaporated and the residue extracted into ethyl acetate. The insoluble N-methylmorpholine hydrochloride salt was removed by filtration. The filtrate was concentrated and hexane (20 ml) was added. Cooling results in crystallization of (2,6-dimethyl-4-nitro)phenyl-3-(3-succinimidyloxy-carbonyl) propyloxy-9,10-dihydro-N-methyl-acridan-9-carboxylate. The crystals were finally filtered and washed with hexane (yield=70%). MS: FAB, dithiothreitol/dithioerythrytol matrix, 588 (M++1). HPLC: Waters $C_{18}$ Novapak (3.9 mm×15 mm) (commercially available from Millipore Corporation, Waters Chromatography Division, Milford, Mass.), $CH_3CN/H_2O$ (0.1% trifluoracetic acid) 60:40, flow rate 1.0 ml/min, retention time 6.34 min, detected at 280 nm.

EXAMPLE 3

Another structure encompassed by the invention is (2,6-dimethyl-4-nitro) phenyl-N-methyl-acridinium-9-carboxylate-3-oxo-butyrimidate chloride, hydrochloride which has the following formula:

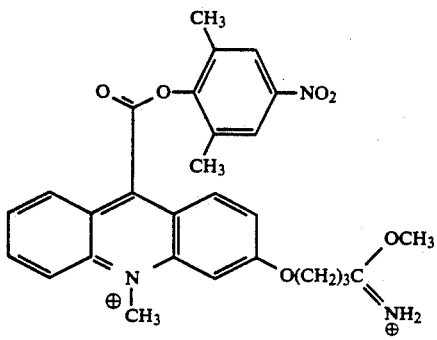

The compound (2,6-dimethyl-4-nitro)phenyl-N-methyl-acridinium-9-carboxylate-3-oxo-butyrimidate chloride, hydrochloride is synthesized according to the following scheme:

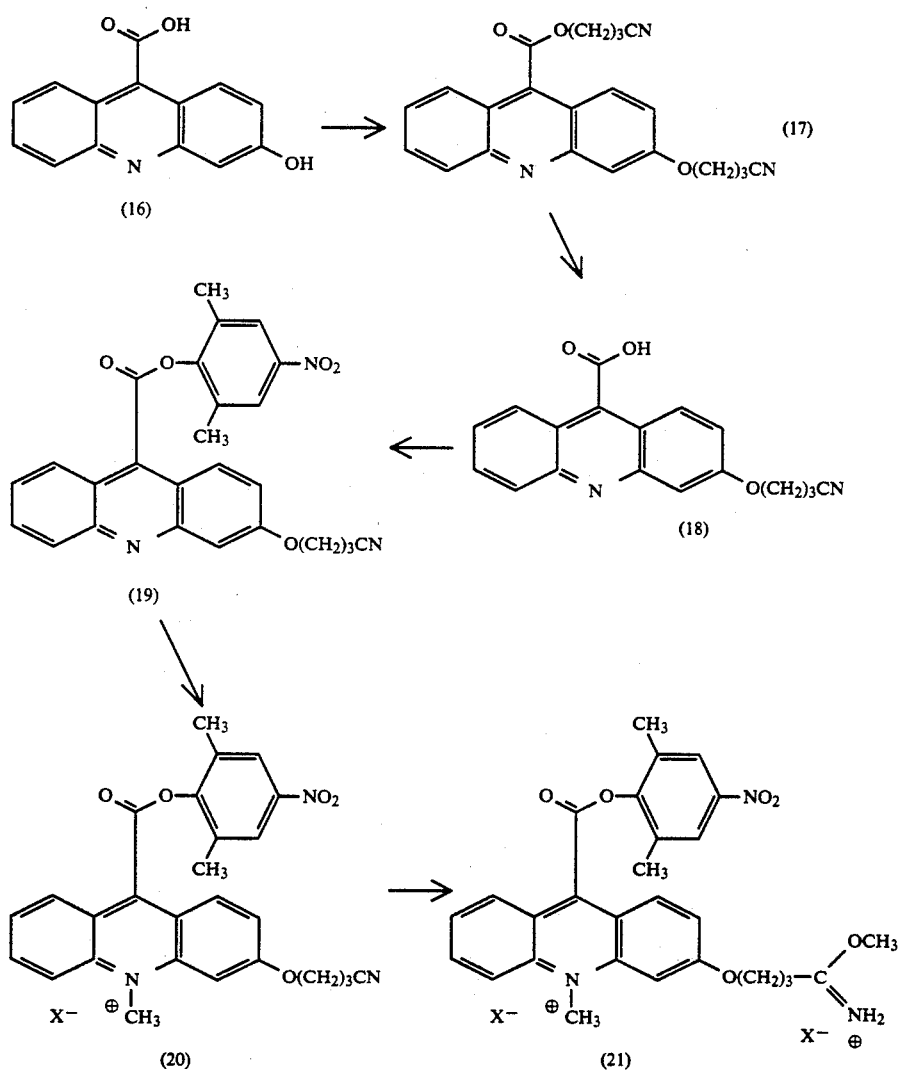

Reaction of 3-hydroxy-9-acridine carboxylic acid (16) with 4-bromobutyronitrile gives an ester (17). Hydrolysis of the ester and reesterification with 2,6-dimethyl-4-nitrophenol provides (19). Methylation with methyl fluorosulfate and conversion of the cyano group to the imidate ester using hydrogen chloride gas and methanol provides (2,6-dimethyl-4-nitro)phenyl-N-methyl-acridinium-9-carboxylate-3-oxo-butyrimidate chloride, hydrochloride (21). These reaction are described in further detail in the following.

In this reaction, 3-hydroxy-9-acridine carboxylic acid (16) (2 g, 8.4 mmole), 4-bromobutyronitrile (5.87 ml, 8.74 g, 34 mmole) and cesium carbonate (11.08 g, 34 mmole) were dissolved in anhydrous DMSO (50 ml) in a 100 ml round bottom flask. The mixture was warmed to about 50° C. in a water bath with stirring. After 3 hours the mixture was poured into water (600 ml). The solids were filtered and were dissolved in chloroform. Drying and evaporation of the solvent gave 3-(3-cyano)propoxyl-acridine-9-carboxylic acid-(3-cyano)-propyl ester (17). It was then dissolved in toluene (50 ml) and cyclohexane (150 ml) was added. The pure product (17) separated, and was then filtered and dried. The dried product was purified by thin layer chromatography with ethylacetate as the mobile phase ($R_f=0.58$) (yield=78.6%).

The cyanopropyl ester (17) (3.73 g. 10 mmoles) was dissolved in a mixture of 0.5N NaOH (90 ml) and methanol (90 ml) and stirred in a water bath at 60° C. using a reflux condenser for 2.5 hours. The methanol was removed in a rotary evaporator and the product was extracted with ethyl acetate after acidifying the aqueous phase with concentrated hydrochloric acid. Drying and evaporation of the solvent provides 3-(3-cyano)propoxyl-acridine-9-carboxylic acid (18) (yield=80%).

The carboxylic acid (18) (4.62 g, 15 mmole) was dissolved in pyridine (130 ml) and the solution was cooled in a CCl$_4$/dry ice bath. Para toluenesulfonyl chloride (5.8 g, 30 mmole) was added and the bath was removed. After 15 minutes of stirring at room temperature, 2,6-dimethyl-4-nitrophenol (2.8 g, 16.8 mmole) was added. After 18 hours at room temperature, water (10 ml) was added and the solvents were removed in vacuo. The residue was dissolved in chloroform (200 ml) and the organic layer was washed with saturated sodium bicarbonate (2×100 ml), water (2×100 ml), 1N HCl (1×100 ml) and finally with water (2×100 ml). Drying and evaporation of the solvent gave (2,6-dimethyl-4-nitro)-phenyl-3-(3-cyano) propoxyl-acridine-9-carboxylate (19) which was chromatographed in a silica gel column using ethylacetate/hexane (7:3) as solvent (yield=74.5%).

The ester (19) (1.6 g, 3.52 mmole) was dissolved in dry methylene chloride (50 ml) and under nitrogen methyl fluorosulfate (1.6 ml, 17.6 mmole) was added. The solution was stirred at room temperature for 20 hours. Anhydrous ether (100 ml) was added and the precipitated (2,6-dimethyl-4-nitro)phenyl-3-(3-cyano)-propoxyl-acridinium-9-carboxylate fluorosulfonate (20) was filtered, washed with ether and dried in vacuo (yield=84.7%).

The acridinium ester (20) (4 mg, 7.4×10$^{-3}$ mmole) was dissolved in methanol (0.5 ml) in a 5 ml 2-necked flask. Anhydrous hydrogen chloride gas was bubbled carefully for 10 minutes. Anhydrous ether (3 ml) was added. The precipitated (2,6-dimethyl-4-nitro)phenyl-N-methyl-acridinium-9-carboxylate-3-oxo-butyrimidate chloride, hydrochloride (21) was collected and washed with ether. The solid was dried in vacuum and was stored in a dessicator containing phosphorus pentoxide.

EXAMPLE 4

The compound (2,6-dimethyl-4-trimethylammonio)-phenyl-N-methyl-acridinium-9-carboxylate difluorosulfonate has the following formula:

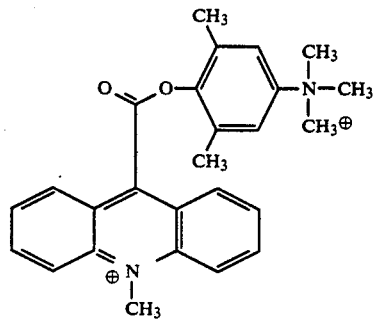

This compound, (2,6-dimethyl-4-trimethylammonio)-phenyl-N-methyl-acridinium-9-carboxylate difluorosulfonate, was synthesized according to the following scheme:

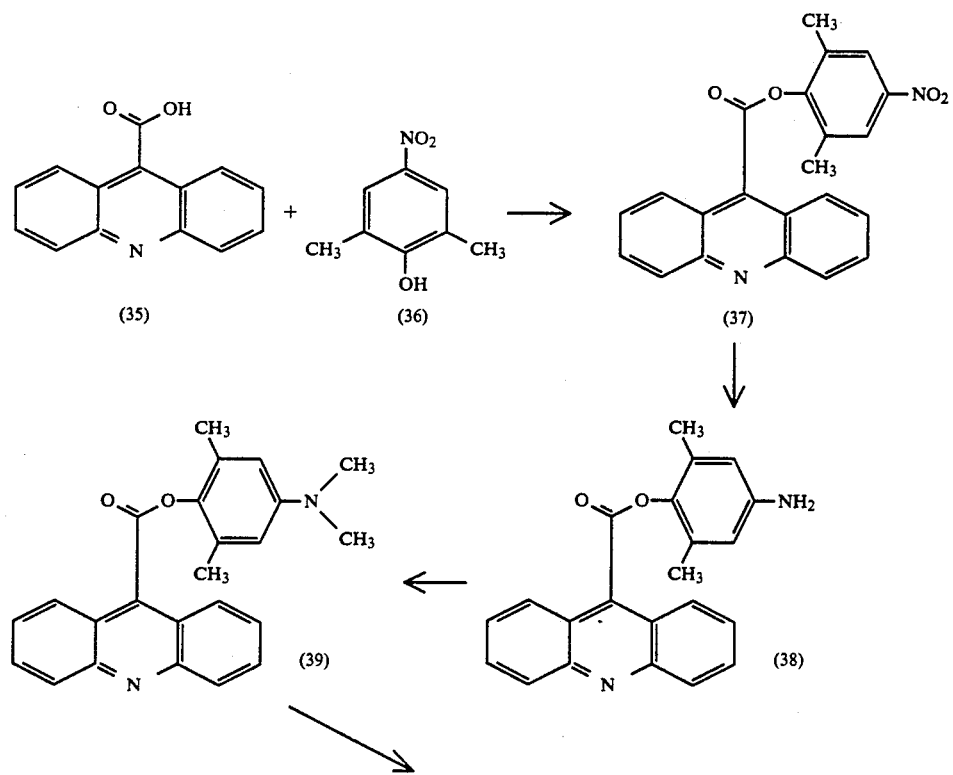

-continued

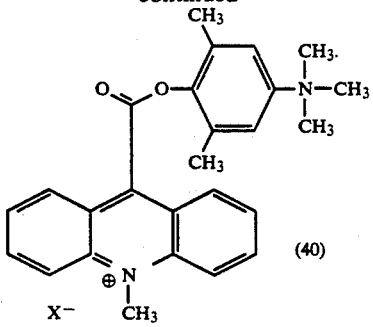

In the reaction scheme, (2,6-dimethyl-4-trimethylammonio)phenyl-N-methyl-acridinium-9-carboxylate (40) was obtained by esterification of acridine-9-carboxylic acid (35) with 2,6-dimethyl-4-nitrophenol (36). The product (37) was reduced to the (2,6-dimethyl-4-amino)phenyl-acridine-9-carboxylate (38) with zinc. Two methyl groups were introduced on the amino group by treatment with methyl iodide. Quaternization and acridinium formation was then accomplished using methyl fluorosulfate. These reactions are described in further detail in the following.

Acridine-9-carboxylic acid (35) (3.05 g, 0.014 moles) in a 250 ml round bottom flask was mixed with thionyl chloride (65 ml) and the mixture was refluxed for 2 hours with stirring. The excess thionyl chloride was removed in a rotary evaporator. The residue was treated with benzene (75 ml) and the solvent was removed in vacuo to remove traces of thionyl chloride. The residue of acridine-9-carbonyl chloride was mixed with pyridine (65 ml) and 2,6-dimethyl-4-nitrophenol (36) (2.25 g, 0.014 moles) was added. The mixture was warmed using a water bath (about 60° C.) to dissolve all the solids. After 15 hours of stirring at room temperature the mixture was poured into 1 liter of water. The suspension was acidified with concentrated hydrochloric acid to pH 2.0. The solid product was filtered, washed with water and dissolved in chloroform. Drying (anhydrous sodium sulfate) and evaporation of chloroform gave the crude ester.

The crude ester was chromatographed on a silica gel column using $CHCl_3$/EtOAc 98:2 as solvent. The fractions with $R_f$ value of 0.6 on TLC with the same solvent were pooled and evaporation of the solvents gave pure (2,6-dimethyl-4-nitro)phenyl-acridine-9-carboxylate (37) (yield=30%).

The (2,6-dimethyl-4-nitro)phenyl ester (37) (1.16 g, 3.1 mmol) was dissolved in acetic acid (50 ml) by warming in an oil bath at about 65° C. Stannous chloride (1.5 g) was dissolved in concentrated hydrochloric acid (10 ml) and was added to the ester solution. The mixture was stirred for 45 minutes and was then poured into water (750 ml). Extraction with chloroform (3×200 ml) removed unreacted (2,6-dimethyl-4-nitro)phenyl ester. The aqueous layer was made basic with sodium bicarbonate and was extracted with chloroform (4×200 ml). Drying and evaporation of the chloroform gave (2,6-dimethyl-4-amino)phenyl-acridine-9-carboxylate (38) (yield=25%).

The amino ester (38) (64 mg, 0.18 mmole) was dissolved in nitromethane (5 ml). Methyl iodide (1 ml) and pyridine (0.1 ml) were added. The mixture was stirred at room temperature for 15 hours. Methanol (2 ml) was added and the mixture was then stirred for an additional 2 hours. The solvents were evaporated and the residue was treated with water (10 ml) and was then extracted with chloroform (4×20 ml) after the solution was made basic. Drying and evaporation of the chloroform gave (2,6-dimethyl-4-dimethylamino)phenyl-acridine-9-carboxylate (39) (yield=50%).

The dimethylamino ester (39) (154 mg. 0.41 mmole) was dissolved in methylene chloride (2 ml). Methyl fluorosulfate (265 1, 3.28 mmole) was added and the mixture was stirred at room temperature for 15 hours. Amhydrous ether (15 ml) was added and the precipitated solids were filtered and washed with ether. Drying gave (2,6-dimethyl-4-trimethylammonio) phenyl-N-methyl-acridinium-9-carboxylate (40) (yield=50%). MS: FAB, thioglycerol matrix, m/e 400 (M+).

EXAMPLE 5

The compound 3-(2-carboxyethyl)-N-methyl acridinium (2,6-dimethyl-4-nitrophenyl)-9-carboxylate trifluoromethyl sulfonate (N-hydroxy succinimidyl ester), has the formula:

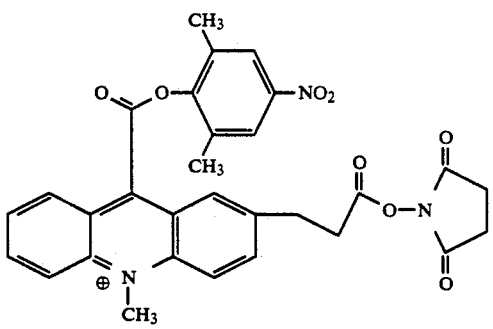

It is made as follows: 4-bromocinnamic acid (Aldrich Chemical Company) (2 g.) was suspended in methanol (10 ml) and platinum oxide (100 mg) was added. The solution was stirred for 4 hours in a hydrogen atmosphere, and the solvent was removed to give a colorless oil (1.8 g, 84%) ms (m/e) 244 (M+), 211,184,121.

nmr (ppm) 7.34, 7.32, 7.07, 7.04. (2 doublets, 4H) 3.31, (3H, singlet) 2.80, 2.57 (multiplets, 4H).

In the reaction, 4-Bromopropionic acid (5 g) was mixed with formanilide (2.25 g), anhydrous $K_2CO_3$ and copper bronze (150 mg) in nitrobenzene (17 ml). The mixture was refluxed for 48 hours and the nitrobenzene then removed under vacuum. The resulting brown oil was reflexed in a mixture of acetic acid and conc. HCl (1:1). Extraction into ether, and evaporation of the dried ether solution gave a dark green oil which solidified on standing. The solid was washed with petroleum ether to give a white solid (5 g, 67%) ir 1703 (CO) 3403 (NH) ms (m/e) 241 (M+), 196,182,167.

The previous compound (1.5 g) in carbon disulfide (8 ml) was added slowly over ten minutes to a refluxing solution of oxalyl chloride (1.07 g) in carbon disulfide (6 ml), and refluxing continued for a further one hour. The mixture was evaporated to dryness and carbon disulfide (12 ml) was added. Aluminum chloride (2.88 g) was added in portions, with stirring, and the reaction refluxed for one hour. After removing the solvent, water was added and the product extracted into ether. A red oil was obtained which solidified on standing. (1.3 g, 76%). ir 1734,1677 cm$^{-1}$ (CO) nmr (ppm). The spectra clearly showed the presence, in almost equal amounts, of two isomers. There is no need to separate them, as they both give the same product in the next stage. Peaks at 7.66 to 6.79 (aromatic protons, 8H) multiplets 3.02 to 2.89 (two methylene groups, 4H).

The previously obtained mixture of isatins (1 g) was dissolved in 10% aqueous KOH and refluxed for 18 hours. A yellow precipitate was obtained by acidifying the cooled solution with conc. HCl. The precipitate was collected by filtration and washed with water, methanol and ether (700 mg, 76%) ir (nujol) 1711, 1656 (CO) uv (nm) 388, 370, 358, 340 and 256 nmr (ppm) 12 (broad, 1H) 8.20, 2.18, 8.16, 8.14, 8.13 (2H) 8.06, 8.03 (2H) 7.90, 7.88, 7.84, 7.83 (1H) 3.01, 3.08, 3.06 (2H) 2.07, 2.68, 2.66 (2H)

Analysis: Found (%) C 66.76, H 5.32, N 4.42. $C_{17}H_{13}NO_4$ requires C 66.86, H 5.57, N 4.11.

The acridine carboxylic acid prepared in the previous step (20 mg) was suspended in re-distilled thionyl chloride (2 ml) and reflexed under an argon atmosphere for 4 hours. The solid (ir 1793 and 1731 cm$^{-1}$ COCl) which resulted after the removal of the thionyl chloride was dissolved in pyridine (1 ml) and N-hydroxy succinimide (6.92 mg) was added. The reaction mixture was stirred under an argon atmosphere for 4 hours, and then cooled in an ice bath. Para-toluene sulfonyl chloride (21.36 mg) was added, and after stirring for 15 minutes, 2,6-dimethyl-4 nitrophenol was added. The reaction was left for 2.5 hours and the pyridine was removed under high vacuum. A few drops of dilute HCl were added and the resulting precipitate was collected by filtration and washed with water and dried (18 mg, 60%). ir (Nujol) 1812, 1781 and 1740 cm$^{-1}$ (CO) uv (nm) 373, 353 and 262. Addition of base caused the hydrolysis of the phenol, giving peaks at 430, 392, 355 and 257.

The acridine ester was dissolved in dichloromethane (2 ml) and methyl triflate (0.5 ml) added. After stirring over night at room temperature, the volatile materials were removed under vacuum, and the residue dissolved in acetonitrile. A yellow solid was precipitated on the addition of ether. ir (Nujol) 1812,1785 and 1745 cm$^{-1}$ uv (MeOH, nm) 369, 354 and 262. Addition of base gave peaks at 430 (p-nitrophenolate) 364, 287 and 257 nm. Thus confirming the structure of 3-(2-Carboxyethyl)-N-methyl acridinium (2,6-dimethyl-4-nitrophenyl)-9-carboxylate trifluoromethyl sulfonate (N-hydroxy succinimidyl ester).

EXAMPLE 6

The compound 3-(2-carboxyethyl (N-methyl acridinium (2,6-dimethyl-4-nitrophenyl)-9-carboxylate trifluoromethyl sulfonate 2,6-dimethyl-4-nitrophenyl ester has the formula:

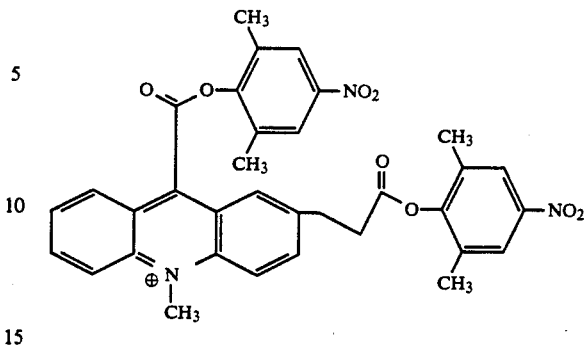

It is made as follows: 3-(2-carboxyethyl) acridine 9-carboxylic acid (20 mg) was dissolved in pyridine (0.5 ml) and the solution cooled in an ice bath. Then p-toluene sulfonyl chloride (51 mg) was added and the solution stirred for 15 minutes. 2,6-Dimethyl-4-nitrophenyl (23 mg) was added and the reaction mixture stirred for 2.5 hours at room temperature. Ice and dilute HCl were added and the resulting yellow precipitate filtered off. Washing with water, ethanol and ether gave a yellow solid (26 mg, 65%). The following analysis was obtained:

ir (nujol) Carbonyl peak at 1746 cm$^{-1}$.

uv (MeOH, HCl) 365, 348, 285 (sh), 262 nm.

ms (m/e) 594 (M+1), 445, 427, 390.

The above diester (25 mg) was suspended in dichloromethane (2 ml) and freshly distilled methyl triflate (0.1 ml) added. The solution became clear dark yellow after 30 minutes. After 18 hours, dry ether was added to the solution, resulting in a yellow precipitate. This was collected by filtration (28 mg, 88%). Its analysis showed:

ir (nujol) Strong carbonyl peak at 1752 cm$^{-1}$.

uv (MeOH) (acid) 368, 353, 263 nm. (base) 430, 364, 287, 257 nm.

Thus confirming the compound 3-(2-Carboxyethyl(N-methyl acridinium (2,6-dimethyl-4-nitrophenyl)-9-carboxylate trifluoromethyl sulfonate 2,6-dimethyl-4-nitrophenyl ester.

The above diester, possessing as it does of a moderately hindered active ester, is suitable for labeling for the analytical purposes described elsewhere in this application. Labeling of the TSH antibody was carried out as previously described, to give labelled antibody with a specific activity substantially identical to that using the previously described esters, resulting in an equivalent immunoassay.

EXAMPLE 7

The compound 2,6-dimethyl-4-nitrophenyl-2-(2-[N-(2,6 dimethyl-4-chlorosulfonyl) phenyl] carboxamidoethyl-N-methylacridinium-9-carboxylate fluorosulfonate has the following formula:

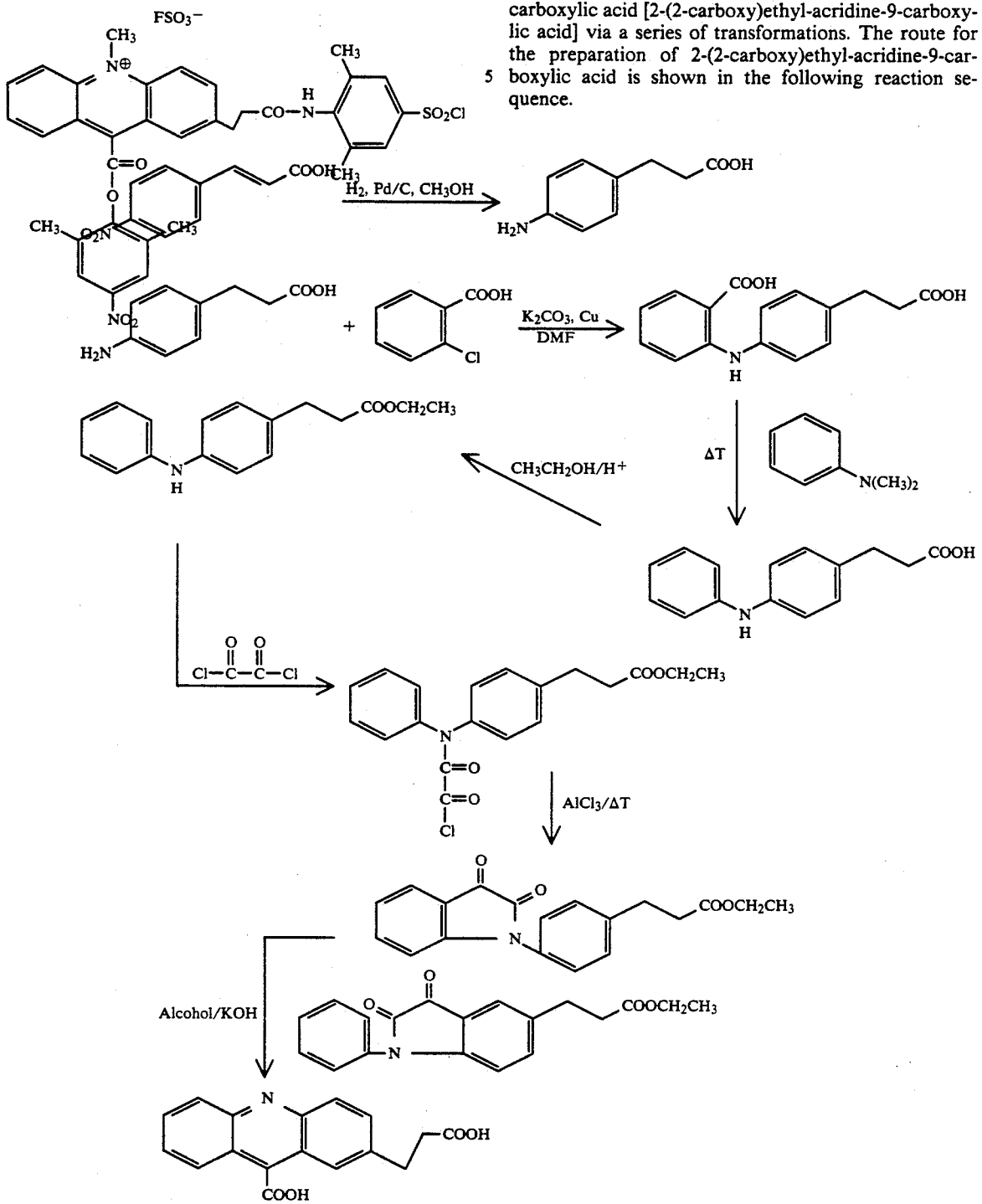

This compound is synthesized from the acridine dicarboxylic acid [2-(2-carboxy)ethyl-acridine-9-carboxylic acid] via a series of transformations. The route for the preparation of 2-(2-carboxy)ethyl-acridine-9-carboxylic acid is shown in the following reaction sequence.

The route for the preparation of 2,6-dimethyl-4-nitrophenyl-2-[2-(2,6-dimethyl-4-chlorosulfonylphenylcarbamyl)ethyl]-N-methylacridinium-9-carboxylate fluorosulfonate, title compound of this example, is detailed in the following reaction sequence.

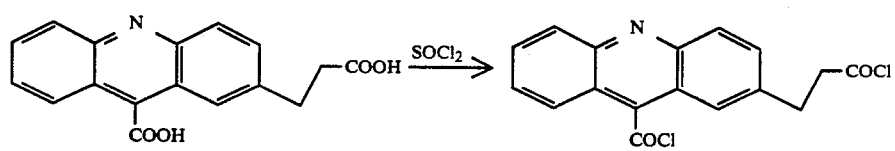
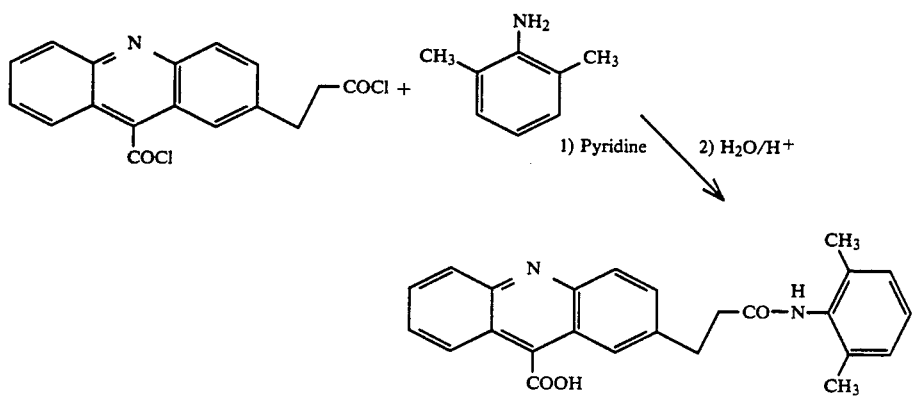
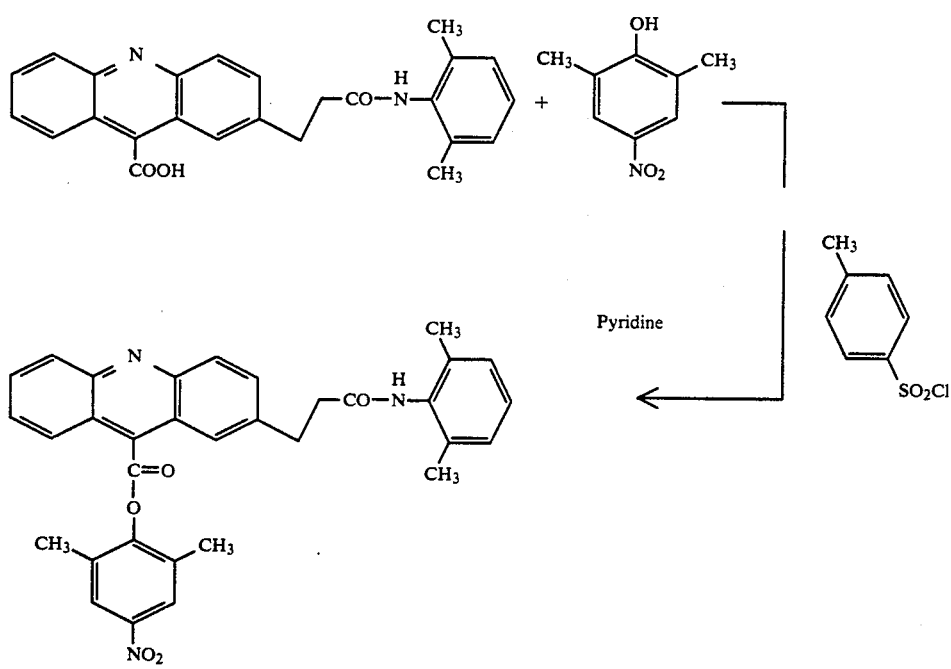
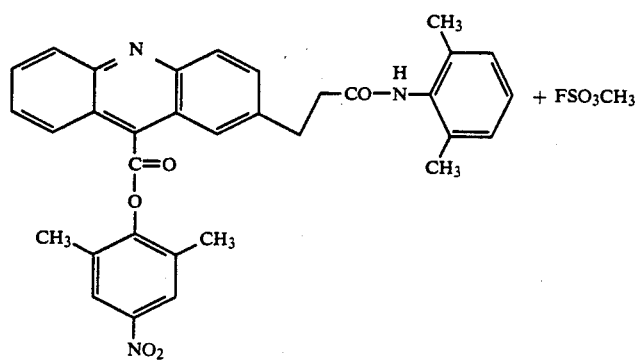

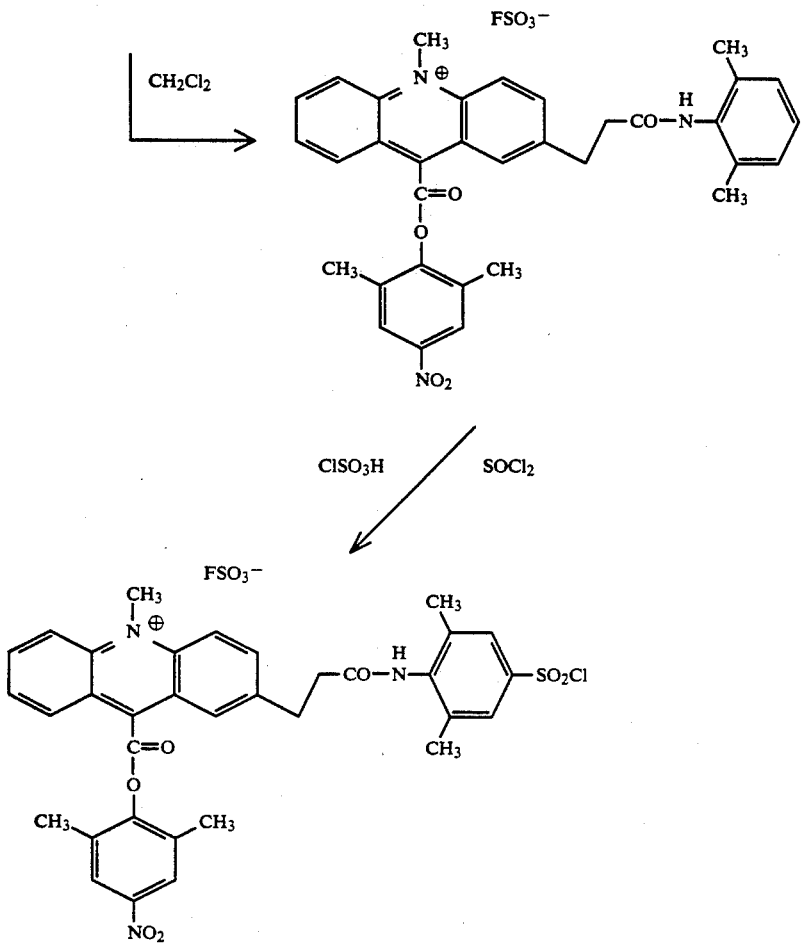

The compositions, p-aminophenylpropionic acid, N-[4-(2-carboxyethyl)]anthranilic acid, N-phenyl-4-aminophenylpropionic acid and ethyl-N-phenyl-4-aminophenylpropionate, were prepared according to the first reaction sequence and all were isolated, purified and characterized by IR, N.R.M.S. and U.V.

The isatin that was prepared from N-phenyl-ethyl-p-aminophenylpropionate in two steps, as shown in the first reaction sequence of this Example, resulted in two isomers. They were identified by NMR and IR. The data is as follows:

NMR(360 MH$_2$, FT, CD$_3$OD, d PPM): 7.66 ppm to 6.79 ppm (aromatic protons), —CH$_2$ from 4.13 ppm to 4.04 ppm (as multiplet), —CH$_2$ from 3.02 ppm to 2.89 ppm (as two multiplets), another—CH$_2$ (as two triplets) from 2.68 ppm to 2.60 ppm and—CH$_3$ as multiplet from 1.23 ppm to 1.18 ppm.

The compound 2-(2-carboxy)ethylacridine-9-carboxylic acid was prepared from the isatin isomers, as indicated above, in aqueous potassium hydroxide solution. The yield was over 76%. Its characterization is obtainable from the following:

NMR (360MH$_2$FT, DMSO, d); [8.20 ppm, 8.17 ppm, 8.15 ppm, 8.14 ppm, 8.12] (2H), [8.05 ppm, 8.03 ppm] (d,2H), [7.90 ppm, 7.88 ppm, 7.84 ppm, 7.83 ppm] (1H), [3.10 ppm, 3.08 ppm, 3.06 ppm] (t,2H), [2.70 ppm, 2.68 ppm, 2.66 ppm] (t,2H) and a broad peak at 12 ppm (—H).

M.S.(FAB): m/e 296 (M$^+$+1) IR(nujol) carbonyl peaks at 1711 cm$^{-1}$ and 1656 cm$^{-1}$. U.V. (MeOH) 388 nm, 370 nm, 358 nm, 340 nm, 256 nm, in acid at 362 nm, 346 nm and 272 nm.

| Microanalysis for C$_{17}$H$_{13}$NO$_4$. C$_2$H$_5$OH | | | |
|---|---|---|---|
| | C% | H% | N% |
| Expected | 66.86 | 5.57 | 4.11 |
| Found | 66.76 | 5.32 | 4.42 |

The compound 2-(2-carboxy)ethyl acridine-9-carboxylic acid was chlorinate with thionyl chloride to give the corresponding acid chloride using the procedures described in the preceeding examples.

To a solution of the diacid chloride (200 mg., 0.602 mmoles) in pyridine (4 ml.), 2,6-dimethyaniline (73 mg., 0.603 mmoles) was added. The reaction was stirred at room temperature (23° C.) for 23 hours. After addition of H$_2$O/H$^+$, compound precipitated out, which was filtered, dried and washed with ether. Compound 2-[2-(2,6-dimethyl-phenylcarbamoyl)ethyl]acridine-9-carboxylic acid in over 90% yield, was obtained. Its analysis showed: M.S.(FAB): m/e 399 (M$^+$+1) IR (nujol): carbonyl peak at 1651 cm$^{-1}$.

This compound was converted to 2,6-dimethyl-4-nitrophenyl-2-[2-(2,6-dimethylphenylcarbamoyl) ethyl]acridine-9-carboxylate

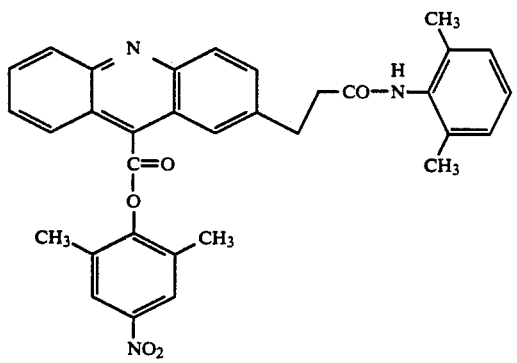

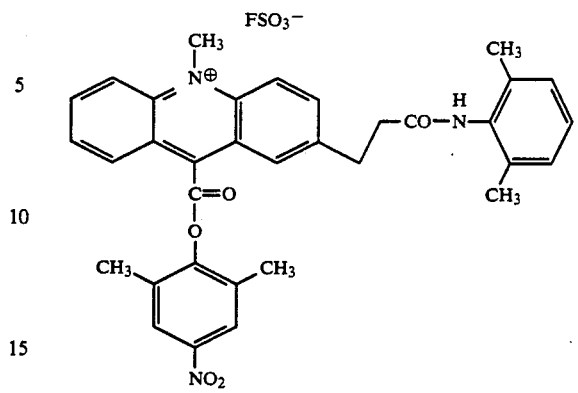

by Brewster's method with over 70% yield. The compound was purified by chromatography. The analysis showed: UV (MeOH) in H+p; 368 nm, 350 nm, 264 nm and in base, at 430 nm, 392 nm, 363 nm and 256 nm. IR (nujol): carbonyl peaks at 1748 cm.$^{-1}$ and 1659 cm.$^{-1}$ NMR (500 MH$_z$, CDCl$_3$, 5): aromatic protons from 8-4523 ppm to 6.6123 ppm, two triplets at [3.39 ppm, 3.37 ppm, 3.36 ppm], (2H), [2.91 ppm, 2.89 ppm, 2.88 ppm], (2H), a singlet at 2.52 ppm (6H) and another singlet at 2.03 ppm (6H).

N-methylation of the compound

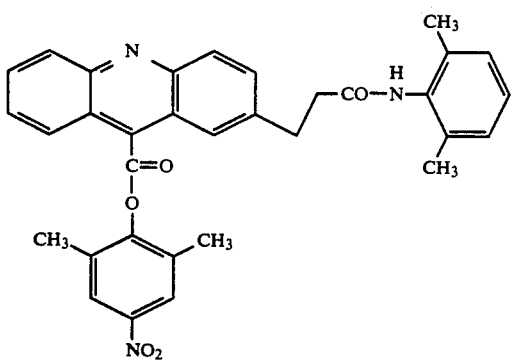

with methyl fluorosulfonate, resulted, 2,6-dimethyl-4-nitrophenyl-2[2-(2,6-dimethylphenylcarbamoyl)ethyl]-N-methylacridinium-9-carboxylate with over 80% yield. Its structure was supported by the following data: M.S. (FAB), 562 m/e (m++1) U.V.(MeOH) in H+, shows peaks at 374 nm, 355 (sh), 266 nm, in OH, at 430 nm, 330 nm (sh), 185 nm, 252 nm.

The compound was converted to 2,6-dimethyl-4-nitrophenyl-2-[2-(2,6-dimethyl-4-chlorosulfonyl-phenylcarbamoyl)ethyl]-N-methylacridinium-9-carboxylate fluorosulfonate in chlorosulfonic acid and thionylchloride with over 70% yield. Analysis: M.S. (FAB): 660 m/e (m++1) U.V.-(MeOH) in H+, shows peaks at 373 nm, 356 nm, 266 nm, in OH, at 425 nm, 288 nm, 255 nm.

EXAMPLE 8

The following procedure for attaching to protein is generally applicable to chemiluminescent labels of the present invention.

Mouse IgG (Sigma, 1 mg) was dissolved in 0.9 ml phosphate buffer (100 mM, pH 8.0, 150 mM). If desired, higher pH may be employed, such as a pH as high as 9.5. The solution was then divided into three equal portions of 0.33 mg/0.3 ml (0.0022 µmoles). About 0.3 mg of a moiety of the present invention was dissolved in about 0.4 ml DMF so as to obtain 0.022 moles of moiety in 15 µl DMF.

0.022 µmoles of the compound of the present invention was mixed with 0.0022 µmoles of IgG in a plastic microcentrifuge tube. After 15 minutes, an additional 0.022 µmoles of compound was added to the microcentrifuge tube (compound to protein molar ratio was 20:1). After an additional 15 minutes, excess amounts of the compound of the present invention were quenched with lysine HCl solution (10 µl in 100 mM p/buffer, pH 8.0) for 15 minutes.

Alternatively, aliquots of 0.0055 µmoles of the compound of the present invention was used instead of 0.022 µmoles (compound to protein molar ratio was 5:1).

Biorad glass columns (1 cm×50 cm) (commercially available from Biorad, Chemical Division, Richmond, Calif.) were packed with previously swelled and deaerated Sephadex G-50-80 in phosphate buffer (100 mM, pH 6.3, 150 mM NaCl, 0.001% TMS) to a bed volume of 45 ml. The reaction solution was run through the columns at a flow rate of 0.3-0.4 ml/min. 0.5 ml fractions were collected. Labelled protein fractions were detected by diluting 20 µl from each fraction to 1 ml and determining the chemiluminescence produced with 30 µl of the diluted solution. Labelled fractions were then pooled.

The pooled conjugate fractions were dialyzed to improve the purity of immunoreactive conjugate. The pooled fractions were dialyzed against 500 ml pH 6.3 phosphate buffer (100 mM, pH 6.3, 150 mM NaCl, 0.001% TMS) over a period of 24 hours with three buffer changes.

GENERAL LABELING PROCEDURE FOR SULFONYL CHLORIDE BASED ACRIDINIUM ESTERS.

Anti-TSH antibody (1 mg) is transferred to a Centricon 30 (ultrafiltration unit, Amicon, Beverly, MA) and 1 ml bicarbonate buffer (15 mM, pH 9.6) is added. The buffer is centrifuged and the volume of solution brought up to 400 μl using the same buffer. A solution of the compound of the formula

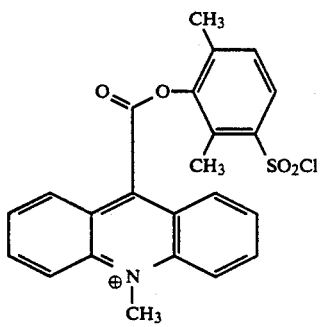

in DMF (N,N-dimethylformamide, 2 mg/mL, 21.6 μl) is added to the anti-TSH antibody and the Centricon is gently mixed for 15 minutes by hand. Another 21.6 μl from a freshly made DMF solution of the same compound, is added at the end of 15 minutes. A total of 24 moles pf the compound to antibody, is used in the reaction. Fifteen minutes from the second addition, the protein solution is purified from the unreacted compound using a Sephadex desalting column (Pharmacia HR-10/10), an HPLC system, and a eluent solvent comprising 1 part ethanol and 4 parts phosphate buffer (100 mM sodium phosphate, 300 mM sodium chloride, pH 6.0). The protein fraction is collected and the eluent solvent is exchanged with phosphate buffer (pH 6.3) in a Centricon 30. The concentrate acridinium labelled anti-TSH antibody is diluted into 25 ml of diluent buffer (sodium phosphate buffer 100 mM, sodium chloride 150 mM, Thimerosal 0.001%, 0.4% BSA, 0.1 mg/ml each (0.001%) of mouse and goat γ-globulins, pH 6) after filtration through a 0.45 micron syringe filter. The diluted 25 milliliters is stored at $-20°$ C. as a stock solution to make TSH labelled antibody reagent after appropriate dilutions.

Assay Protocols

EXAMPLE 9

1. Components

A) Labelled Antibody (conjugate): Affinity purified rabbit antiprolactin conjugated to (2,6-dimethoxy-3-chlorosulfonyl)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 μg/ml) as a solid phase on Nunc ® tubes (commercially available from Midland Scientific, Roseville, Minn.).

C) Solid-phase coated tubes: Dried Nunc ® tubes were prepared as follows:
1) 0.3 ml of the capture antibody per tube at 6 μg/ml in PBS buffer (phosphate buffer saline, pH 7.2–7.4, 10 mM phosphate, 100 mM NaCl, 10 mM NaN$_3$) was pipetted into Nunc ® tubes.

2) Tubes were incubated for 18–24 hours.
3) Tubes were washed 2 times with the PBS buffer.
4) Tubes were blocked with 2.0% BSA in PBS buffer. Incubate for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum 0, 5, 30, 100 and 200 ng/ml/ml

2. Assay Protocol 1) 25 μl of sample or standard was pipetted into the antibody-coated tubes. 2) 100 μl of labelled antibody was added. 3) Tubes were vortexed gently. 4) Tubes were incubated for 1 hour at room temperature on a rotator. 5) Tubes were washed 3 times with deionized water. 6) Chemiluminescence was counted for 2 seconds [pump 1: 0.1N HNO$_3$+0.25% H$_2$O$_2$; pump 2: 0.25N NaOH +0.125% CTAC] in a LumaTag ™ Analyzer (commercially available from London Diagnostics, Eden Prairie, Minn.).

EXAMPLE 10

1. Components

A) Progesterone Conjugate of a b-D-thioglucose adduct of (2,6-dimethoxy-3-chlorosulfonyl)phenyl-N-methyl-acridinium-9-carboxylate fluorosulfonate: 20 pg/ml progesterone conjugate in phosphate buffer (pH 6.0, 100 mM phosphate, 150 mM NaCl, 0.1% human serum albumin, 0.001% Thimerosal).

B) Primary antibody: Rabbit anti-progesterone (Cambridge Medical Diagnostics) in phosphate buffer (pH 6.0, 200 mM phosphate, 150 mM NaCl, 0.1% human serum albumin, 0.01% CHAPS, 5 μg Danazol).

C) Solid-phase coated tubes: Dried Nunc ® tubes coated with 2.5 μg of Goat anti-Rabbit fc and blocked with 0.5% BSA. Tubes were prepared as follows:
1) Tubes were incubated for 1 hour with 2.5 μg/ml Goat anti-Rabbit fc (500 μl) at room temperature.
2) Tubes were washed 3 times with distilled water.
3) Tubes were immediately incubated for 3 hours with 0.5% BSA (500 μl) at room temperature.
4) Tubes were washed 3 times with distilled water.
5) Tubes were dried overnight at 40% relative humidity at room temperature.
6) Tubes were stored in plastic freezer bags at 4° C.

D) Serum matrix: Antech steer serum.

E) Standards: 0, 0.13, 0.38, 1.31, 7.31 16.6 and 37.0 ng/ml.

2. Assay Protocol 1) 50 μl of sample or standard was pipetted into the antibody-coated tubes.
2) 100 μl of conjugate buffer was added.
3) 100 μl of primary antibody buffer was added.
4) Tubes were vortexed gently.
5) Tubes were incubated for 2 hours at 37° C.
6) Tubes were decanted and washed with 150 mM NaCl in 0.1% Tween (1 ml) and then 3 times with distilled water.
7) Tubes were inverted and allowed to drain.
8) Chemiluminescence was counted for 2 seconds[pump 1: 0.1N HNO$_3$+0.25% H$_2$O$_2$; pump 2: 0.25N NaOH +1.125% CTAC] in a LumaTag ™ Analyzer (commercially available from London Diagnostics, Eden Prairie, Minn.).

EXAMPLE 11

1. Components

A) Labelled Ab: Affinity purified goat anti-TSH conjugated to (2,6-dimethoxy-3-chlorosulfonyl)phenyl-N-methyl-acridinium-9-carboxylate fluorosulfonate.

B) Storage buffer: 100 mM phosphate, 0.145M NaCl, 0.001% Thimerosal, 0.4% BSA, 0.1 mg/ml mouse-globulins, and 0.1 mg/ml goat-globulins, pH 6.0.

C) Capture antibody: Monoclonal-anti-TSH (2 µg/ml) as a solid phase on Nunc ® tubes. Procedure for preparation of solid-phase Nunc ® tubes:

1) 0.4 ml of the capture antibody at 2 µg/ml in PBS buffer (phosphate buffer saline, pH 7.2–7.4, 10 mM phosphate, 100 mM NaCl, 10 mM NaN₃) was added to each tube.
2) Tubes were incubated for 18–24 hours.
3) Tubes were washed 3 times with the PBS buffer.
4) Tubes were blocked with 2.0% BSA in PBS buffer and incubated for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum.0, 0.5, 2.5, 10, 25 and 100 µIU/ml

2. Assay Protocol 1) 200 µl of sample was pipettd into the coated tubes.
2) 100 µl of labelled antibody was added.
3) Tubes were vortexed gently.
4) Tubes were incubated for 2 hours at room temperature on a shaker.
5) Tubes were washed using a Biotomic washer (commercially available from Ocean Scientific, Inc., Garden Grove, Calif.).
6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

EXAMPLE 12

1. Components

A) Labelled Ab: Affinity purified rabbit anti-prolactin conjugated to (2,6-dimethyl-4-nitro)phenyl-N-methyl-acridinium-9-carboxylate fluorosulfonate. Storage buffer: 10 mM phosphate buffer, 100 mM NaCl pH 6.0, 0.001% Thimerosal, 0.4% BSA.

B) Capture antibody: Rabbit anti-prolactin (6 µg/ml) as a solid phase on Nunc ® tubes.

C) Solid-phase coated tubes: Dried Nunc ® tubes were prepared as follows:

1) 0.3 ml of the capture antibody per tube at 6 µg/ml in PBS buffer (phosphate buffer saline, pH 7.2–7.4, 10 mM phosphate, 100 mM NaCl, 10 mM NaN₃) was pipetted into Nunc ® tubes.
2) Tubes were incubated for 18–24 hours.
3) Tubes were washed 2 times with the PBS buffer.
4) Tubes were blocked with 2.0% BSA in PBS buffer. Incubate for <4 hours at room temperature.
5) Tubes were washed 3 times with PBS buffer.
6) Tubes were dried at room temperature.
7) Tubes were stored in plastic freezer bags at 4° C.

D) Standards: Prepared in horse serum 0, 5, 30, 100 and 200 ng/ml/ml

2. Assay Protocol 1) 25 µl of sample or standard was pipetted into the antibody-coated tubes.
2) 100 µl of labelled antibody was added.
3) Tubes were vortexed gently.
4) Tubes were incubated for 1 hour at room temperature on a rotator.
5) Tubes were washed 3 times with deionized water.
6) Chemiluminescence was counted for 2 seconds [pump 1: 0.1N $HNO_3$+0.25% $H_2O_2$; pump 2: 0.25N NaOH+0.125% CTAC] in a LumaTag ™ Analyzer (commercially available from London Diagnostics, Eden Prairie, Minn.).

Labelling Of TSH Antibody With
2,6-dimethyl-4-nitrophenyl-2-[2-(2,6-dimethyl-4-chlorosulfonyl-phenylcarbamoyl)ethyl]-N-methyla-cridinium-9-carboxylate fluorosulfonate Anti-TSH antibody was labelled with the compound

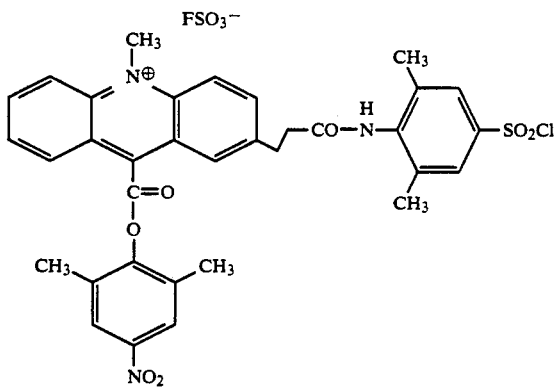

according to the method that is described previously for

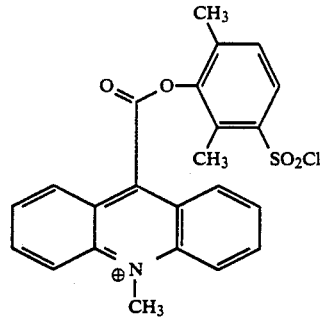

In the reaction, 250 µg (24.7 µl) of Anti-TSH antibody and 2×12 excess moles of the compound were added in 15 minute intervals. At the end the addition, and after purification, the labeled antibody was diluted to 6.25 ml. with the diluent buffer solution and used as stock solution. 100 ml of labeled antibody (stock solution) was diluted with 0.6 ml. of antibody diluent.

TSH assays were carried out using the reagents from a LumaTag ™ TSH kit and substituting the above labeled TSH antibody reagent, comparable results were obtained to that obtained using instead a labeled TSH where the label is the compound of the formula:

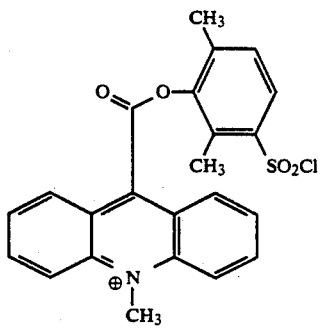

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A chemiluminescent compound possessing an aryl ester, thioester or amide of a carboxylic acid substituted heterocyclic ring or ring system that is susceptible to chemical attack to dissociate the heterocyclic ring to a transient compound: wherein the heterocyclic ring is ring carbon-bonded to the carbonyl of the ester, thioester or amide moiety and possesses a heteroatom in an oxidation state that allows chemiluminescence by dissociating a compound at the carbon bonded to the carbonyl that decays to produce chemiluminescence; the heterocyclic ring or ring system contains bonded to it through an organic moiety, a functional group that is functionally reactive with an active hydrogen containing compound; the aryl ring is a ring or ring system that is ring carbon-bonded to the oxygen, sulfur or nitrogen of the ester, thioester or amide, as the case may be, and contains substituents on a six-member ring that act to sterically and electronically hinder hydrolysis of the ester, thioester or amide linkage; optionally there is an electron donating substituent in a peri position on the heterocyclic ring system; the substituents on the aryl ring comprise at least one ortho electron donating substitution that with the peri substitution comprises at least two substituents adjacent to the ester, thioester or amide linkage that are electron donors; at least one meta or para substituent directly attached to the aryl ring that possesses a $\sigma_p$ value greater than 0 and less than 1.

2. An enhanced hydrolytically stable heterocyclic composition capable of chemiluminescent properties when labeled to an analyte or a specific binding material, by chemically-induced dissociation, comprising (a) an aryl ring,
(b) a sterically-hindered ester, thioester or amide linkage moiety with enhanced hydrolytic stability, and
(c) a heterocyclic organic ring moiety, in which
(1) the carbonyl carbon of (b) is convalently bonded to a carbon atom (x) of (c) and the remaining free valence of (b) is carbon bonded to an aromatic ring carbon atom (y) of (a),
(2) (a) contains at least two substituent groups hindering hydrolysis of (b), at least one of which is electron donating and located on a ring carbon atom adjacent to (y), and a substituent on (a) meta or para to (y) and electron withdrawing with a $\sigma_p$ value greater than 0 and less than 1, and
(3) (c) contains
(i) at least one ring carbon atom adjacent to said ring carbon atom (x), a peri substituent on the ring carbon atom adjacent to said ring carbon atom (x) when there only one substituent on a ring carbon atom adjacent to (y),
(ii) an organic moiety directly bonded thereto that contains a functional group that is functionally reactive with an active hydrogen containing compound, and
(iii) a ring member heteroatom in an oxidation state that provides such chemiluminescence properties.

3. A conjugate possessing chemiluminescent properties by chemical dissociation and enhanced hydrolytic stability, comprising a chemiluminescent label bonded to a specific binding material or analyte, that contains (a) an aryl ring,
(b) a sterically-hindered ester, thioester or amide linkage moiety with enhanced hydrolytic stability, and
(c) a heterocyclic organic ring moiety, in which
(1) the carbonyl carbon of (b) is covalently bonded to a carbon atom (x) of (c) and the remaining free valence of (b) is carbon bonded to an aromatic ring carbon atom (y) of (a),
(2) (a) contains at least two substituent groups hindering hydrolysis of (b), at least one of which is electron donating and located on a ring carbon atom adjacent to (y), and a substituent on (a) meta or para to (y) and electron withdrawing with a $\sigma_p$ value greater than 0 and less than 1, and
(3) (c) contains
(i) at least one ring carbon atom adjacent to said ring carbon atom (x), a peri substituent on the ring carbon atom adjacent to said ring carbon atom (x) when there only one substituent on a ring carbon atom adjacent to (y),
(ii) an organic moiety directly bonded thereto that contains a functional group that is functionally reactive with an active hydrogen containing compound, and
(ii) a ring member heteroatom that is in an oxidation state whereby reaction of molecular oxygen or a peroxide with said composition forms an intermediate which decays to produce chemiluminescence.

4. The chemiluminescent label compound of claim 1 wherein the chemical attack is oxidic or elemental oxygen attack.

5. The chemiluminescent label compound of claim 1 wherein the leaving group includes the aryl ring or ring system.

6. The chemiluminescent label compound of claim 5 wherein the substituent on the six-member ring is one or more groups acting in concert with peri substitution on the heterocyclic ring system to sterically and electronically hinder hydrolysis of the ester, thioester or amide linkage.

7. The conjugate of a specific binding material and the chemiluminescent label compound of claim 1.

8. A conjugate of an analyte and the chemiluminescent label compound of claim 1.

9. A conjugate of a specific binding material and the chemiluminescent label compound of claim 2.

10. A conjugate of an analyte and the chemiluminescent label compound of claim 2.

11. A conjugate of a specific binding material and the chemiluminescent label compound of claim 3.

12. A conjugate of an analyte and the chemiluminescent label compound of claim 3.

13. A conjugate of a specific binding material and the chemiluminescent label compound of claim 5.

14. A conjugate of an analyte and the chemiluminescent label compound of claim 5.

15. A conjugate of a specific binding material and the chemiluminescent label compound of claim 6.

16. A conjugate of an analyte and the chemiluminescent label compound of claim 6.

17. The chemiluminescent label compound of claim 1 having the formula:

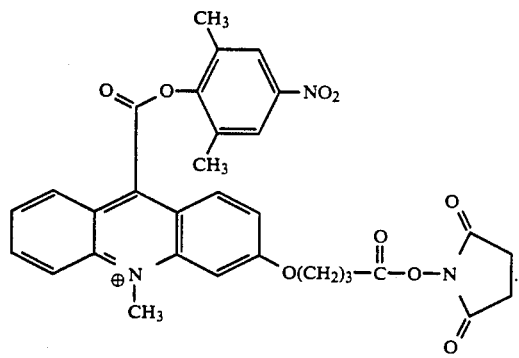

18. The chemiluminescent label compound of claim 1 having the formula:

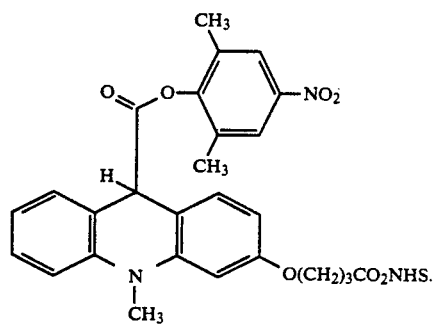

19. The chemiluminescent label compound of claim 1 having the formula:

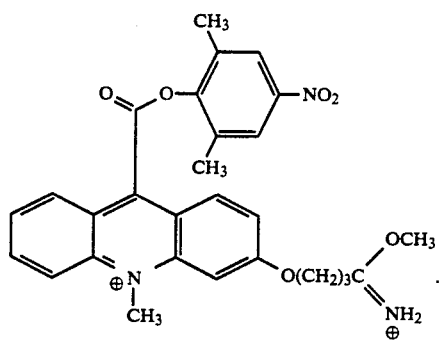

20. The chemiluminescent label compound of claim 1 having the formula:

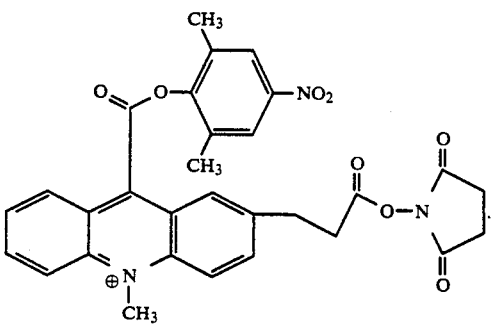

21. The chemiluminescent label compound of claim 1 having the formula:

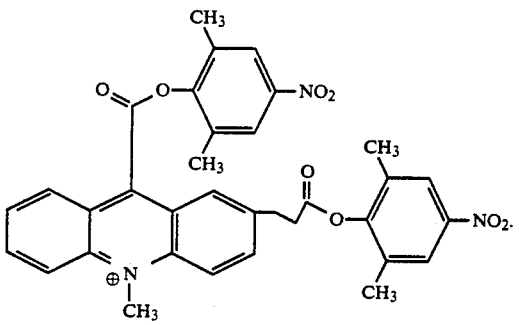

22. The chemiluminescent label compound of claim 1 having the formula:

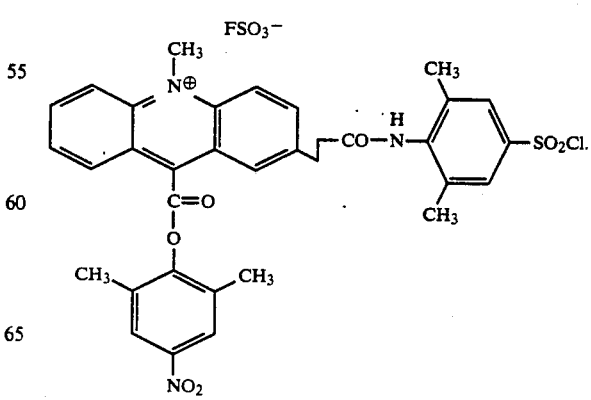

23. A method for assaying the presence of an analyte in a sample which comprises contacting an analyte with the conjugate of claim 7, inducing chemiluminescence by decay of an intermediate dissociated from the conjugate, and measuring luminescence therefrom to assay the analyte.

24. A method for assaying the presence of an analyte in a sample which comprises contacting an analyte with the conjugate of claim 8, inducing chemiluminescence by decay of an intermediate dissociated from the conjugate, and measuring luminescence therefrom to assay the analyte.

25. A method for assaying the presence of an analyte in a sample which comprises contacting an analyte with the conjugate of claim 9, inducing chemiluminescence by decay of an intermediate dissociated from the conjugate, and measuring luminescence therefrom to assay the analyte.

26. A method for assaying the presence of an analyte in a sample which comprises contacting an analyte with the conjugate of claim 10, inducing chemiluminescence by decay of an intermediate dissociated from the conjugate, and measuring luminescence therefrom to assay the analyte.

27. A method for assaying the presence of an analyte in a sample which comprises contacting an analyte with the conjugate of claim 11, inducing chemiluminescence by decay of an intermediate dissociated from the conjugate, and measuring luminescence therefrom to assay the analyte.

28. A method for assaying the presence of an analyte in a sample which comprises contacting an analyte with the conjugate of claim 12, inducing chemiluminescence by decay of an intermediate dissociated from the conjugate, and measuring luminescence therefrom to assay the analyte.

29. A method for assaying the presence of an analyte in a sample which comprises contacting an analyte with the conjugate of claim 13, inducing chemiluminescence by decay of an intermediate dissociated from the conjugate, and measuring luminescence therefrom to assay the analyte.

30. A method for assaying the presence of an analyte in a sample which comprises contacting an analyte with the conjugate of claim 14, inducing chemiluminescence by decay of an intermediate dissociated from the conjugate, and measuring luminescence therefrom to assay the analyte.

31. A method for assaying the presence of an analyte in a sample which comprises contacting an analyte with the conjugate of claim 15, inducing chemiluminescence by decay of an intermediate dissociated from the conjugate, and measuring luminescence therefrom to assay the analyte.

32. A method for assaying the presence of an analyte in a sample which comprises contacting an analyte with the conjugate of claim 16, inducing chemiluminescence by decay of an intermediate dissociated from the conjugate, and measuring luminescence therefrom to assay the analyte.

33. A specific binding assay kit comprising a vial containing a conjugate possessing chemiluminescent properties by chemically induced dissociation and containing the conjugate of claim 7.

34. A specific binding assay kit comprising a vial containing a conjugate possessing chemiluminescent properties by chemically induced dissociation and containing the conjugate of claim 8.

35. A specific binding assay kit comprising a vial containing a conjugate possessing chemiluminescent properties by chemically induced dissociation and containing the conjugate of claim 9.

36. A specific binding assay kit comprising a vial containing a conjugate possessing chemiluminescent properties by chemically induced dissociation and containing the conjugate of claim 10.

37. A specific binding assay kit comprising a vial containing a conjugate possessing chemiluminescent properties by chemically induced dissociation and containing the conjugate of claim 11.

38. A specific binding assay kit comprising a vial containing a conjugate possessing chemiluminescent properties by chemically induced dissociation and containing the conjugate of claim 12.

39. A specific binding assay kit comprising a vial containing a conjugate possessing chemiluminescent properties by chemically induced dissociation and containing the conjugate of claim 13.

40. A specific binding assay kit comprising a vial containing a conjugate possessing chemiluminescent properties by chemically induced dissociation and containing the conjugate of claim 14.

41. A specific binding assay kit comprising a vial containing a conjugate possessing chemiluminescent properties by chemically induced dissociation and containing the conjugate of claim 15.

42. A specific binding assay kit comprising a vial containing a conjugate possessing chemiluminescent properties by chemically induced dissociation and containing the conjugate of claim 16.

* * * * *